United States Patent
Kondo et al.

(10) Patent No.: US 9,598,681 B2
(45) Date of Patent: Mar. 21, 2017

(54) THERMOSTABLE β-XYLOSIDASE BELONGING TO GH FAMILY 3

(71) Applicant: HONDA MOTOR CO., LTD., Minato-Ku, Tokyo (JP)

(72) Inventors: Yasuhiro Kondo, Wako (JP); Jiro Okuma, Wako (JP); Yoshitsugu Hirose, Wako (JP); Asuka Yamaguchi, Wako (JP); Migiwa Suda, Wako (JP); Tomohiko Kato, Kisarazu (JP); Daisuke Shibata, Kisarazu (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 14/854,562

(22) Filed: Sep. 15, 2015

(65) Prior Publication Data

US 2016/0076017 A1   Mar. 17, 2016

(30) Foreign Application Priority Data

Sep. 17, 2014 (JP) ................. 2014-189007

(51) Int. Cl.
| | |
|---|---|
| *C12P 19/14* | (2006.01) |
| *C12N 9/24* | (2006.01) |
| *C12N 9/42* | (2006.01) |
| *C12P 21/06* | (2006.01) |
| *C07H 21/04* | (2006.01) |
| *C07K 1/00* | (2006.01) |
| *C12P 19/02* | (2006.01) |
| *C07K 14/435* | (2006.01) |

(52) U.S. Cl.
CPC .......... *C12N 9/2477* (2013.01); *C07K 14/435* (2013.01); *C12N 9/2445* (2013.01); *C12N 9/2485* (2013.01); *C12P 19/02* (2013.01); *C12P 19/14* (2013.01); *C12Y 302/01037* (2013.01); *C12Y 302/01021* (2013.01)

(58) Field of Classification Search
CPC .. C12N 9/2477; C12N 9/2445; C12N 9/2485; C12P 19/14; C12P 19/02; C07K 14/435; C12Y 302/01037; C12Y 302/01021
USPC ................ 435/99, 200, 209, 69.1; 536/23.2; 530/350
See application file for complete search history.

(56) References Cited

U.S. PATENT DOCUMENTS 7,923,234 B2 * 4/2011 Thompson ..... C12Y 302/01037
                                                                435/200
8,298,795 B2 * 10/2012 Yang ..................... C12N 9/242
                                                                435/162

FOREIGN PATENT DOCUMENTS

| JP | H11-507837 A | 7/1999 |
|---|---|---|
| JP | 11-313683 A | 11/1999 |
| JP | 2011-523346 A | 8/2011 |
| JP | 2013-059272 A | 4/2013 |
| WO | 97/00964 A1 | 1/1997 |
| WO | 2009/094187 A1 | 7/2009 |

OTHER PUBLICATIONS

Banerjee et al., Improving enzymes for biomass conversion: A basic research perspective. Bioenerg. Res., 2010, vol. 3: 82-92.*
Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Guo et al., Protein tolerance to random amino acid change. PNAS., 2004, vol. 101 (25): 9205-9210.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Kormelink et al., "Purification and characterization of three endo-(1,4)-Beta-xylanases and one Beta-xylosidase from Aspergillus awamori", Journal of Biotechnology, Feb. 1993, vol. 27, No. 3, pp. 249-265.
Herrmann et al., "The Beta-D-xylosidase of Trichoderma reesei is a multifunctional Beta-D-xylan xylohydrolase", Biochemical Journal, 1997, vol. 321, pp. 375-381 (printed in Great Britain).
Kitamoto et al., "Sequence Analysis, Overexpression, and Antisense Inhibition of a Beta-Xylosidase Gene, xylA, from Aspergillus oryzae KBN616", Applied and Environmental Microbiology, Jan. 1999, vol. 65, No. 1, pp. 20-24.
La Grange et al., "Degradation of Xylan to D-Xylose by Recombinant Saccharomyces cerevisiae Coexpressing the Aspergillus niger Beta-Xylosidase (xlnD) and the Trichoderma reesei Xylanase II (xyn2) Genes", Applied and Environmental Microbiology, Dec. 2001, vol. 67, No. 12, pp. 5512-5519.

(Continued)

*Primary Examiner* — Ganapathirama Raghu
(74) *Attorney, Agent, or Firm* — Carrier Blackman & Associates, P.C.; Joseph P. Carrier; Fulchand P. Shende

(57) ABSTRACT

A thermostable β-xylosidase, having a β-xylosidase catalytic domain including: (A) a polypeptide including the amino acid sequence represented by SEQ ID NO: 1, 3 or 5, (B) a polypeptide including an amino acid sequence in which at least one amino acid has been deleted, substituted, or added in the amino acid sequence represented by SEQ ID NO: 1, 3 or 5, and having hydrolysis activity against a substrate of p-nitrophenyl-β-D-xylopyranoside at least under conditions of 80° C. and pH 4.0, or (C) a polypeptide including an amino acid sequence having 80% or greater sequence identity with the amino acid sequence represented by SEQ ID NO: 1, 3 or 5, and having hydrolysis activity against a substrate of p-nitrophenyl-β-D-xylopyranoside at least under conditions of 80° C. and pH 4.0.

5 Claims, 6 Drawing Sheets

(56) References Cited

OTHER PUBLICATIONS

Shao et al., "Characterization of a Novel Beta-Xylosidase, XylC, from Thermoanaerobacterium saccharolyticum JW/ SL-YS485", Applied and Environmental Microbiology, Feb. 2011, vol. 77, No. 3, pp. 719-726.

Morais et al., "Functional Association of Catalytic and Ancillary Modules Dictates Enzymatic Activity in Glycoside Hydrolase Family 43 Beta-Xylosidase" Journal of Biological Chemistry, Mar. 16, 2012, vol. 287, No. 12, pp. 9213-9221.

Noguchi et al., "MetaGeneAnnotator: Detecting Species-Specific Patterns of Ribosomal Binding Site for Precise Gene Prediction in Anonymous Prokaryotic and Phage Genomes", DNA Research, pp. 387-396, 2008, vol. 15, No. 6.

Finn et al., "The Pfam protein families database", Nucleic Acids Research Database, 2010, vol. 38, p. D211-D222.

Durbin et al., 'The theory behind profile HMMs. Biological sequence analysis: probabilistic models of proteins and nucleic acids', 1998, Cambridge University Press, Cambridge, United Kingdom.

Search Report corresponding to European Patent Application No. 15185298.5 mailed Feb. 4, 2016.

Rizzatti et al., "Purification and properties of a thermostable extracellular beta-D-xylosidase produced by a thermotolerant Aspergillus phoenicis", Journal of Industrial Microbiology and Biotechnology, Mar. 1, 2001, pp. 156-160, vol. 26, No. 3.

Tsujibo, et al., "Cloning, Sequencing, and Expression of the Gene Encoding an Intracellular Beta-D-Xylosidase from Streptomyces thermoviolaceus OPC-520", Bioscience Biotechnology Biochemistry, Jan. 1, 2001, pp. 1824-1831, vol. 65, No. 8.

Gibbs, et al., "Cloning, Sequencing, and Expression of a Xylanase Gene from the Extreme Thermophile Dictyoglomus thermophilum Rt46B.1 and Activity of the Enzyme on Fiber-Bound Substrate", Applied and Environmental Microbiology, American Society for Microbiology, Dec. 1, 1995, pp. 4403-4408, vol. 61, No. 12, US.

* cited by examiner

FIG. 1

```
AR19M-311-2              1  MEERMQRRVEELLSKMILEEKIAQLGSIPSGKLVE-NGKFESREKAKELLKNGIGQITRVAGYAEREPEESIELI 74
Dictyoglomus thermophilum 1 MEEKELSKKVKDLLAKMILEEKIAQLQAVYGKDLVDENGNFSEEKAEKLLKNGIGQISRVAGERGVSPEKAVELA 75

AR19M-311-2             75  NEIQRFLKEETRLGIPAITHEECLSGMTKGAITFPQAIGMASTFPDDTQRMTSTIRKEMKAFGVHQGLSPVLD 149
Dictyoglomus thermophilum 76 NKIQKFLKEKIRGIPAITHEECGSGFMAQGAIVFPQAIGMASTFPELURRVSDVIRQHLKAANVHQGLSPVLD 150

AR19M-311-2            150  IPRDPRMGRIEETFGEDPYLVSVMAESYIKGLQGEDMKEGIAIAKHFTAVGISEGGRNLGPARVSEREIREVFL 224
Dictyoglomus thermophilum 151 IPRDPRWGRIEETFGEDPYLVSRMATEYMKGLQGEDWREGIVATVKHFTAVGISEGARNLGPAKVGERELREVFL 225

AR19M-311-2            225  FPFEVAIRKANAGSVMNAYHEIDGVPCASSKFLTKIIREEMGFKGFVSDVSDYSATEMLHTEHKVAKDLKTAAIKA 299
Dictyoglomus thermophilum 226 FPFEVAIKEGQAGSIMNAYHEIDGVPCASSKFLTKIIREWENGFKGYVSDYVSDYIAVRMLENFHKVARDAKFAAVLA 300

AR19M-311-2            300  GAGIETELPEIKCYGEPLLSAVKEGKVSMSVIDTAVARVLRAKILGLLDDIIYADPSKIRAVLDNPEHRAFARI 374
Dictyoglomus thermophilum 301 GAGIDIELPSVDCYGEPLIQAVKEGLISEEVLNASVERVLRAKFMLGIFDDNLEKDPKKVYEVFDKPEFRDLSR 375

AR19M-311-2            375  ELARKSIVLIKNDGILPISKGVKTIAVIGPSADSTKNLHGDYSYISHIAGVADG------VRIVTMLEGI 438
Dictyoglomus thermophilum 376 EVARRSIVLIKDGTLPLSKNLKVAVIGPVADNPRNLHGDYSYIAHIPSIAEGLEGVKVEEKCVRTVSILEGI 450

AR19M-311-2            439  KNKVSSGITVLVYAKGCELSDESREGFKEALDTIASRDVILAWGENSGIFKRGISGEGNDRIDLKPGVQEFLK 513
Dictyoglomus thermophilum 451 RNKVSPEIEVLVYAKGCDIISDSKDGFAEAIEMAKEADVTIAWGEESGIFHRGISGEGNDRITTLEIFGVQRDLK 525

AR19M-311-2            514  ALKEVGKPIVLVLVNGRPLSIKMEEKNTPAILEVMPGEEGGNAIADVIFGDVNPGGKLPISEPKDVGQIPWYN 588
Dictyoglomus thermophilum 526 ELHKLGKPIVLVLVNGRPQALKMEHENLNAIIEAMYPGEEGGNAVADVIFGDVNPSGKLPISFPAVTGQLPWYN 600

AR19M-311-2            589  RKPSAFSEYLTTDTKPLPFGHGLSYTTFEYSELKIPENVMPGGYIDLSFKVRNIGNIDGDEVVQLYIHDEMAS 663
Dictyoglomus thermophilum 601 RKPSAFSDYIDESAKPLYPFGHGLSYTTFEYSDLKISPEKVNSLEKVELSFTIKNIGNRDGEEWVQLYIHDQVAS 675

AR19M-311-2            664  VERPIKELKGFKPFLKAREEKVIFRLFTDQLAFYDEVMRFVVEAGTEEVMVGSSSEDIRITGKFEVLETKVLI 738
Dictyoglomus thermophilum 676 LERPVKELKGFKKDYLKPGESKRVIFTLLYPEQLAFYDEFMRFIIVEKGVFEEVVIGSSSEDIRVWGTFEVLETKVLI 750

AR19M-311-2            739  KDRKFASEVTIEP 751
Dictyoglomus thermophilum 751 EKRKFASDVKVE 762
```

FIG. 2

```
AR19M-311      1 MEERWLQRRVEELLSKMTLEEKIAQLGSIPSGKLVENGKFSREKAKELLKNGIGQITRVAGYAEREPEESIELINEIQRF  80
AR19M-311-2    1 ................................................................................  80
AR19M-311-11   1 ................................................................................  80

AR19M-311     81 LKEETRLGIPAIIHEECLSGVMTKGATTFPQAIGMASTFEPDDIQRMTSIIRKEMKAFGVHQGLSPVLDIPRDPRWGRTE 160
AR19M-311-2   81 ................................................................................ 160
AR19M-311-11  81 ................................................................................ 160

AR19M-311    161 ETFGEDPYLVSKMAESYIKGLQGEDMREGIIATVKHFTAYGISEGRRNLGPARVSERELREVFLPFEVAIRKANAGSVM 240
AR19M-311-2  161 ........................K.........A..........G................................ 240
AR19M-311-11 161 ........................K.........A..........G................................ 240

AR19M-311    241 NAYHEIDGVPCASSKFLLTKILREEWGFKGFVVSDYSAIEMLHTFHKVAKDLKTAAIKALEAGIETELPEKKCYGEPLLS 320
AR19M-311-2  241 ............................................................I................. 320
AR19M-311-11 241 ............................................................I................. 320

AR19M-311    321 AVKEGKVSVSVIDTAVARVLRAKILLGLLDDIIYVDPSKIRAVLDNPEHRAFARELARKSIVLLKNDGILPISKGVKTIA 400
AR19M-311-2  321 ...............................A................................................ 400
AR19M-311-11 321 ...............................A................................................ 400

AR19M-311    401 VIGPSADSTKNLHGDYSYTSHIAGVADGVRTVTVLEGIKNKVSSGTTVLYAKGCELSDESREGFKEALDIASRSDVIIAV 480
AR19M-311-2  401 ................................................................................ 480
AR19M-311-11 401 ................................................................................ 480

AR19M-311    481 MGENSGLFKRGISGEGNDRIDLKLPGVQEELLKALKEVGKPIVLVLVNGRPLSIKWEKENIPAILEVWYPGEEGGNAIAD 560
AR19M-311-2  481 ................................................................................ 560
AR19M-311-11 481 ................................................................................ 560

AR19M-311    561 VIFGDYNPGGKLPISFPKDVGQIPVYYNRKPSAFSEYLTTDKPLFPFGHGLSYTTFEYSELKIIPENVMPGGYVDISFK 640
AR19M-311-2  561 ................................................................................ 640
AR19M-311-11 561 ................................................................................ 640

AR19M-311    641 VRNTGNIDGDEVVQLYIHDEWASVERPIKELKGFKRIHLKAREEKKVTFRLFTDQLAFYDEVMRFVVEAGTFEVMVGSSS 720
AR19M-311-2  641 ................................................................................ 720
AR19M-311-11 641 ................................................................................ 720

AR19M-311    721 EDIRLTGKFEVLETKVITKDRKFASEVIIEP 751
AR19M-311-2  721 ............................... 751
AR19M-311-11 721 ............................... 751
```

AR19M-311-2

AR19M-311-11

THERMOSTABLE β-XYLOSIDASE BELONGING TO GH FAMILY 3

TECHNICAL FIELD

The present invention relates to a thermostable β-xylosidase, a polynucleotide encoding the thermostable β-xylosidase, an expression vector for expressing the thermostable β-xylosidase, a transformant into which the expression vector has been incorporated, and a method for producing a lignocellulose degradation product using the thermostable β-xylosidase.

Priority is claimed on Japanese Unpublished Patent Application No. 2014-189007, the content of which is incorporated herein by reference.

BACKGROUND ART

In recent years, as a result of concerns related to energy supplies for transportation, as well as other environmental problems such as global warming and aerial pollution, the development of alternative energy sources to oil has become an extremely important issue. Plant biomass is the most plentiful renewable energy source on earth, and holds great promise as an alternative energy source to oil. The main component of plant biomass is lignocellulose, which is composed of polysaccharides such as celluloses and hemicelluloses (including xylan, arabinan and mannan), and lignin. These polysaccharides are hydrolyzed by a large variety of glycoside hydrolases to form monosaccharides such as glucose and xylose, which can then be used as biofuels or the raw materials for chemical products.

Lignocellulose is recalcitrant due to its highly complex structure, and is difficult to degrade or hydrolyze with a single cellulolytic enzyme. Accordingly, among the various polysaccharides, hydrolysis of cellulose generally requires three types of glycoside hydrolase enzymes, namely an endoglucanase (endo-1,4-β-D-glucanase, EC 3.2.1.4), an exo-type cellobiohydrolase (1,4-β-cellobiosidase or cellobiohydrolase, EC 3.2.1.91, EC 3.2.1.176), and a β-glucosidase (EC 3.2.1.21). On the other hand, the structure of hemicellulose varies depending on the plant, and for example in the case of hardwoods and herbaceous plants, xylan is the main structural component. Hydrolysis of xylan requires a xylanase (endo-1,4-β-xylanase, EC 3.2.1.8) and a β-xylosidase (3.2.1.37). β-xylosidase is a hydrolase involved in the process of hydrolyzing the oligosaccharides generated by hydrolysis of the hemicellulose by xylanase to produce monosaccharides.

In conventional bioethanol production using lignocellulose as a starting resource, hydrolysis processes using high solid loading (30 to 60% solid loading) have been tested with the aim of achieving a more energy-efficient conversion to ethanol. However, in this type of lignocellulose enzymatic hydrolysis using high solid loading, the viscosity of the biomass slurry is high, and the hydrolysis reaction of the lignocellulose tends to proceed poorly. Accordingly, by using a thermostable enzyme and performing the enzymatic hydrolysis treatment at a high temperature of 80° C. or higher, the rate of the hydrolysis reaction can be increased, and the viscosity of the biomass slurry can be reduced, which is expected to enable a shortening of the hydrolysis reaction time and a reduction in the amount of enzyme required. As a result, for all of the various glycoside hydrolases, the development of enzymes having superior thermostability is very desirable.

Many thermostable glycoside hydrolases have been obtained by isolating and identifying thermophilic microorganisms that exist in high-temperature environments, cloning genes from these isolated and cultured microorganisms, determining the DNA sequence, and then expressing the DNA using *E. coli* or filamentous fungi or the like. For example, Patent Document 1 discloses a β-xylosidase derived from a filamentous fungus. Patent Document 2 discloses a β-xylosidase derived from the filamentous fungus *Aspergillus oryzae*, the β-xylosidase exhibiting enzymatic activity at 30° C. Patent Document 3 discloses a β-xylosidase derived from *Alicyclobacillus acidocaldarius*, the β-xylosidase exhibiting enzymatic activity at pH 5.5 or lower and temperatures of 50° C. or higher. Patent Document 4 discloses a β-xylosidase derived from *Acremonium cellulolyticus*, the β-xylosidase exhibiting enzymatic activity at 45° C. Further, Non-Patent Documents 1 to 6 disclose β-xylosidases isolated from specific bacteria and filamentous fungi, including β-xylosidases having an optimum temperature in the vicinity of 60° C.

PRIOR ART LITERATURE

Patent Documents

Patent Document 1: Published Japanese Translation No. Hei 11-507837 of PCT
Patent Document 2: Japanese Unexamined Patent Application, First Publication No. Hei 11-313683
Patent Document 3: Published Japanese Translation No. 2011-523346 of PCT
Patent Document 4: Japanese Unexamined Patent Application, First Publication No. 2013-59272

Non-Patent Documents

Non-Patent Document 1: Kormelink et al., Journal of Biotechnology, 1993, vol. 27, pp. 249 to 265.
Non-Patent Document 2: Herrmann et al., Biochemical Journal, 1997, vol. 321, pp. 375 to 381.
Non-Patent Document 3: Kitamoto et al., Applied and Environmental Microbiology, 1999, vol. 65, pp. 20 to 24.
Non-Patent Document 4: La Grange et al., Applied and Environmental Microbiology, 2001, vol. 67, pp. 5512 to 5519.
Non-Patent Document 5: Shao et al., Applied and Environmental Microbiology, 2011, vol. 77, pp. 719 to 726.
Non-Patent Document 6: Morais et al., Journal of Biological Chemistry, 2012, vol. 287, pp. 9213 to 9221.

SUMMARY OF THE INVENTION

Problems to be Solved by the Invention

The present invention has an object of providing a novel thermostable β-xylosidase that exhibits hydrolysis activity against a substrate of p-nitrophenyl-β-D-xylopyranoside (hereafter often abbreviated as PNPX) at least under conditions of 80° C. and pH 4.0, a polynucleotide encoding the thermostable β-xylosidase, an expression vector for expressing the thermostable β-xylosidase, a transformant into which the expression vector has been incorporated, and a method for producing a lignocellulose degradation product using the thermostable β-xylosidase.

Means for Solving the Problem

In order to achieve the above object, the inventors of the present invention extracted DNA directly from the high-temperature soils of hot springs, and by carrying out a large-scale metagenomic sequencing of the microbial flora that was difficult to culture, they succeeded in obtaining a thermostable β-xylosidase having a novel amino acid sequence, thus enabling them to complete the present invention.

In other words, a thermostable β-xylosidase, a polynucleotide, an expression vector, a transformant, a method for producing the thermostable β-xylosidase, a glycoside hydrolase mixture, and a method for producing a lignocellulose degradation product according to the present invention have the aspects [1] to [10] described below.

[1] A thermostable β-xylosidase, having a β-xylosidase catalytic domain including:

(A) a polypeptide including the amino acid sequence represented by SEQ ID NO: 1, 3 or 5, (B) a polypeptide including an amino acid sequence in which at least one amino acid has been deleted, substituted, or added in the amino acid sequence represented by SEQ ID NO: 1, 3 or 5, and having hydrolysis activity against a substrate of p-nitrophenyl-β-D-xylopyranoside at least under conditions of 80° C. and pH 4.0, or (C) a polypeptide including an amino acid sequence having 80% or greater sequence identity with the amino acid sequence represented by SEQ ID NO: 1, 3 or 5, and having hydrolysis activity against a substrate of p-nitrophenyl-β-D-xylopyranoside at least under conditions of 80° C. and pH 4.0.

[2] The thermostable β-xylosidase according to [1], which also exhibits β-glucosidase activity.

[3] A polynucleotide, having a region encoding a β-xylosidase catalytic domain, the region including:

(a) a nucleotide sequence encoding a polypeptide including the amino acid sequence represented by SEQ ID NO: 1, 3 or 5, (b) a nucleotide sequence encoding a polypeptide which includes an amino acid sequence in which at least one amino acid has been deleted, substituted, or added in the amino acid sequence represented by SEQ ID NO: 1,3 or 5, and has hydrolysis activity against a substrate of p-nitrophenyl-β-D-xylopyranoside at least under conditions of 80° C. and pH 4.0, (c) a nucleotide sequence encoding a polypeptide which includes an amino acid sequence having 80% or greater sequence identity with the amino acid sequence represented by SEQ ID NO: 1, 3 or 5, and has hydrolysis activity against a substrate of p-nitrophenyl-β-D-xylopyranoside at least under conditions of 80° C. and pH 4.0, (d) a nucleotide sequence, having 80% or greater sequence identity with a nucleotide sequence represented by SEQ ID NO: 2, 4 or 6, and encoding a polypeptide that has hydrolysis activity against a substrate of p-nitrophenyl-β-D-xylopyranoside at least under conditions of 80° C. and pH 4.0, or (e) a nucleotide sequence of a polynucleotide which hybridizes with a polynucleotide including the nucleotide sequence represented by SEQ ID NO: 2, 4 or 6 under stringent conditions, the nucleotide sequence encoding a polypeptide having hydrolysis activity against a substrate of p-nitrophenyl-β-D-xylopyranoside at least under conditions of 80° C. and pH 4.0.

[4] The polynucleotide according to [3], wherein the polypeptide also exhibits β-glucosidase activity.

[5] An expression vector incorporating the polynucleotide according to [3] or [4], the expression vector being capable of expressing a polypeptide having β-xylosidase activity in a host cell.

[6] A transformant into which the expression vector according to [5] has been introduced.

[7] The transformant according to [6], which is a eukaryote.

[8] A method for producing a thermostable β-xylosidase, the method including generating the thermostable β-xylosidase in the transformant according to [6] or [7].

[9] A glycoside hydrolase mixture, including the thermostable β-xylosidase according to [1] or [2], a thermostable β-xylosidase encoded by the polynucleotide according to [3] or [4], or a thermostable β-xylosidase produced by the method for producing a thermostable β-xylosidase according to [8], and at least one other glycoside hydrolase.

[10] A method for producing a lignocellulose degradation product, the method including generating the lignocellulose degradation product by bringing a material composed of lignocellulose containing cellulose, hemicellulose and lignin a material containing lignocellulose into contact with the thermostable β-xylosidase according to [1] or [2], a thermostable β-xylosidase encoded by the polynucleotide according to [3] or [4], the transformant according to [6] or [7], a thermostable β-xylosidase produced by the method for producing a thermostable β-xylosidase according to [8], or the glycoside hydrolase mixture according to [9].

Effects of the Invention

The thermostable β-xylosidase according to the present invention has hydrolysis activity against a substrate of p-nitrophenyl-β-D-xylopyranoside (hereafter often abbreviated as PNPX) at least under conditions of 80° C. and pH 4.0. For this reason, the thermostable β-xylosidase is suitable for hydrolysis processes of materials containing lignocellulose under high-temperature conditions, and for example is ideal for a hydrolysis process of a lignocellulose-containing material containing hemicellulose or cellulose.

Further, in another aspect of the present invention, the thermostable β-xylosidase is suitable for hydrolysis processes of compounds having β-xylosidic bonds under high-temperature conditions, and is particularly ideal for hydrolysis processes of materials containing oligosaccharides having β-xylosidic bonds.

Furthermore, in yet another aspect of the present invention, the thermostable β-xylosidase is suitable for hydrolysis processes of compounds having β-glycosidic bonds under high-temperature conditions, and is particularly ideal for hydrolysis processes of materials containing oligosaccharides having β-glycosidic bonds.

Moreover, the polynucleotide according to the present invention, an expression vector incorporating the polynucleotide, and a transformant into which the expression vector has been introduced can be used favorably in the production of the thermostable β-xylosidase according to the present invention.

BRIEF DESCRIPTION OF THE DRAWINGS

FIG. 1 is an amino acid sequence alignment diagram of the amino acid sequence (SEQ ID NO: 1) of the β-xylosidase gene clone AR19M-311-2, and the amino acid sequence (SEQ ID NO: 10) of a β-xylosidase belonging to the GH3 family of *Dictyoglomus thermophilum*.

FIG. 2 is an amino acid sequence alignment diagram of the amino acid sequence (SEQ ID NO: 1) of the open reading frame AR19M-311, the amino acid sequence (SEQ ID NO: 3) of the AR19M-311-2 protein, and the amino acid sequence (SEQ ID NO: 5) of the AR19M-311-11 protein.

DETAILED DESCRIPTION OF THE INVENTION

Thermostable β-Xylosidase 1

Figure 3A:
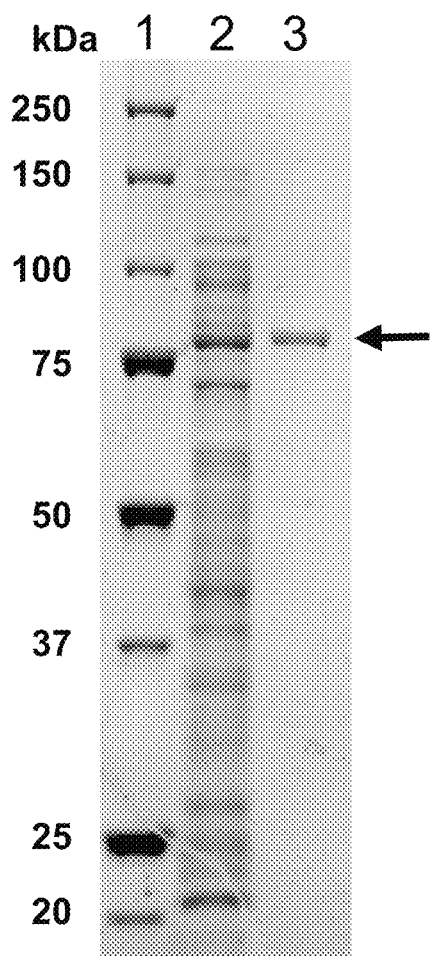
FIG. 3A is a diagram showing the SDS-PAGE analysis results in Example 1 of the AR19M-311-2 protein obtained by expressing the AR19M-311-2 gene in *E. coli* (left).

Many microorganisms including filamentous fungi, bacteria and Archaea are difficult to culture, and it is said that 99% of the microorganisms inhabiting microbial environments such as soil are still unknown. In particular, the culturing of microorganisms that exist in high-temperature environments is extremely difficult, and it is thought that only a mere 0.1% or less of the microorganisms that exist in soils have been able to be isolated and cultured with currently available microbial culturing techniques. This difficulty in culturing microorganisms from high-temperature soils is one of the reasons hindering the development of thermostable enzymes.

In recent years, as a result of the development of next generation giga sequencers that enable a large amount of sequencing of giga base pairs, whole genome sequencing of the microbial flora contained in soils or the like has become possible. By using this analysis technology, the metagenomic analysis method has been proposed, in which the genomic DNA of a microbial group is prepared from an environmental sample such as soil, the genomes of the group having non-uniform and miscellaneous genomic compositions are sequenced directly and comprehensively, and the sequenced data are assembled by a parallel computer, thereby reconstructing the genomic sequences of the microbial flora. This method has contributed to rapid progress in the genome sequencing of microorganisms that are difficult to culture.

As shown in Example 1 described below, the inventors of the present invention extracted the genomic DNA (metagenomic DNA) of microbial groups from collected high-temperature hot spring soils (for example, hot spring water of 58 to 78° C. containing soil, mud, biomat and biofilm and the like), and conducted shotgun sequencing and annotation of the metagenomic DNA, thus obtaining 406 open reading frames (ORFs) encoding amino acid sequences similar to known β-glucosidase enzymes or β-xylosidase enzymes (namely, amino acid sequences having an expectation value (E-value) of less than $1e^{-20}$). For each of the full-length ORFs for which a β-glucosidase catalytic domain or a β-xylosidase catalytic domain was confirmed, a primer was designed based on the nucleotide sequence information of the ORF, and gene candidates were cloned from the metagenomic DNA of the high-temperature hot spring soils by the PCR method. The PCR-cloned DNAs were incorporated into *E. coli*, and proteins encoded by these nucleotide sequences were expressed, and subjected to functional screening by PNPX degradation activity assay. Finally, two thermostable β-xylosidases AR19M-311-2 and AR19M-311-11 having PNPX degradation activity were obtained from these ORFs. The amino acid sequence of AR19M-311-2 is represented by SEQ ID NO: 3, the nucleotide sequence encoding the amino acid sequence of AR19M-311-2 is represented by SEQ ID NO: 4, the amino acid sequence of AR19M-311-11 is represented by SEQ ID NO: 5, and the nucleotide sequence encoding the amino acid sequence of AR19M-311-11 is represented by SEQ ID NO: 6.

As shown below in Example 1, AR19M-311-2 exhibits a high level of hydrolysis activity against PNPX, and also exhibits hydrolysis activity against p-nitrophenyl-β-D-glucopyranoside (PNPG). On the other hand, AR19M-311-2 exhibits almost no degradation activity against phosphoric acid swollen Avicel (hereafter often abbreviated as PSA), the crystalline cellulose Avicel, carboxymethyl cellulose (hereafter often abbreviated as CMC), laminarin composed of β-1,3- and β-1,6-linked glucan, lichenan composed of β-1,3- and β-1,4-linked glucan, and xylan. This substrate specificity suggests that AR19M-311-2 is a glycoside hydrolase which has at least β-xylosidase activity.

In the present description, one aspect of the β-xylosidase activity is hydrolysis activity against a PNPX substrate.

Further, in the present description, one aspect of the β-glucosidase activity is hydrolysis activity against a PNPG substrate.

Furthermore, in the present description, the expression "has activity" or "exhibits activity" means that the enzyme acts against at least one substrate, with a significant difference occurring in the amount of reducing ends or the color development reaction of the hydrolyzed substrate compared with a negative control.

Accordingly, the expression "has β-xylosidase activity" means that the enzyme acts at least against a PNPX substrate, and generates a significant difference in the amount of reducing ends or the color development reaction of the hydrolyzed substrate compared with a negative control.

Similarly, the expression "has β-glucosidase activity" means that the enzyme acts at least against a PNPG substrate, and generates a significant difference in the amount of reducing ends or the color development reaction of the hydrolyzed substrate compared with a negative control.

Further, in a separate aspect, the expression "has β-xylosidase activity" means that the enzyme acts at least against a compound having β-xylosidic bonds, and preferably a substrate containing an oligosaccharide having β-xylosidic bonds, and generates a significant difference in the amount of reducing ends or the color development reaction of the hydrolyzed substrate compared with a negative control.

Furthermore, in yet another aspect, the expression "has β-xylosidase activity" means that the enzyme acts at least against a compound having β-glucosidic bonds, and preferably a substrate containing an oligosaccharide having β-glucosidic bonds, and generates a significant difference in the amount of reducing ends or the color development reaction of the hydrolyzed substrate compared with a negative control.

When the amino acid sequence of AR19M-311-2 was searched against a database of known amino acid sequences, the amino acid sequence that showed the highest sequence identity was that of a β-xylosidase (Genbank registration ID: YP_002250567.1) (SEQ ID NO: 10) belonging to the GH3 family of *Dictyoglomus thermophilum*, and the sequence identity (homology) was 70%. From the substrate specificity and the sequence identity of the amino acid sequence with that of known proteins, it is clear that AR19M-311-2 is a novel β-xylosidase belonging to the GH3 family.

AR19M-311-2 has hydrolysis activity against a PNPX substrate (namely, β-xylosidase activity) at least under conditions of 80° C. and pH 4.0. Actually, as shown below in Example 1<10>, under conditions of pH 4.0, AR19M-311-2 exhibits xylosidase activity within a broad temperature range from 30 to 90° C. The xylosidase activity of AR19M-311-2 expressed using *E. coli* as a host increases with increasing temperature within a range from 30 to 80° C., but then decreases with increasing temperature within a range from 80 to 100° C. Further, the PNPX degradation activity of AR19M-311-2 exhibits an optimum temperature of $T_{opt}$=80° C., and a melting temperature of $T_m$=82.7° C., and is thus a thermostable β-xylosidase having high thermostability rivaling known β-xylosidases. The optimum pH for the PNPX degradation activity of AR19M-311-2 is pH 4.0, but the enzyme exhibits xylosidase activity across a broad range from pH 3.5 to pH 8.0.

Generally, in a protein having some form of bioactivity, one or a plurality of amino acids can be deleted, substituted, or added, without impairing the bioactivity. In other words, in AR19M-311-2, one or a plurality of amino acids can be deleted, substituted, or added without impairing the glycoside hydrolysis activity including the β-xylosidase activity.

Hence, the thermostable β-xylosidase according to the present invention is a thermostable glycoside hydrolase having a β-xylosidase catalytic domain including any of the following (A) to (C):

(A) a polypeptide including the amino acid sequence represented by SEQ ID NO: 1, 3 or 5, (B) a polypeptide including an amino acid sequence in which at least one amino acid has been deleted, substituted, or added in the amino acid sequence represented by SEQ ID NO: 1, 3 or 5, and having hydrolysis activity against a substrate of PNPX at least under conditions of 80° C. and pH 4.0, or (C) a polypeptide including an amino acid sequence having 80% or greater sequence identity with the amino acid sequence represented by SEQ ID NO: 1, 3 or 5, and having hydrolysis activity against a substrate of PNPX at least under conditions of 80° C. and pH 4.0.

In the present description, a "polypeptide in which an amino acid is deleted" means a polypeptide in which a portion of the amino acids which constitute the polypeptide is missing (removed).

In the present description, a "polypeptide in which an amino acid is substituted" means a polypeptide in which an amino acid which constitutes the polypeptide has been replaced with a different amino acid.

In the present description, a "polypeptide in which an amino acid is added" means a polypeptide in which a new amino acid has been inserted within the polypeptide.

In the aforementioned polypeptide of (B), the number of amino acids deleted, substituted, or added in the amino acid sequence represented by SEQ ID NO: 1, 3 or 5 is preferably 1 to 20, more preferably 1 to 10, and still more preferably 1 to 5.

In the aforementioned polypeptide of (C), the sequence identity with the amino acid sequence represented by SEQ ID NO: 1, 3 or 5 is not specifically limited as long as it is 80% or greater but less than 100%, but the sequence identity is preferably 85% or greater but less than 100%, more preferably 90% or greater but less than 100%, still more preferably 95% or greater but less than 100%, and most preferably 98% or greater but less than 100%.

The sequence identity (homology) between a pair of amino acid sequences is determined by juxtaposing the two amino acid sequences, while inserting gaps in some parts of the sequences to account for insertions and deletions, so as to achieve the best match between corresponding amino acids, and then calculating the proportion of matched amino acids relative to the whole amino acid sequences, excluding gaps, in the resulting alignment. The sequence identity between a pair of amino acid sequences can be determined using a variety of homology search software well known in the art. The sequence identity value between amino acid sequences in the present invention is obtained by calculation on the basis of an alignment obtained from the publicly known homology search software BLASTP.

The aforementioned polypeptides of (B) and (C) may be artificially designed, or may be homologs of AR19M-311-2 or the like, or partial proteins thereof.

Each of the aforementioned polypeptides of (A) to (C) may be chemically synthesized based on the amino acid sequence, or may be generated by a protein expression system using the polynucleotide according to the present invention described below. Further, each of the polypeptides of (B) and (C) can also be artificially synthesized based on the polypeptide including the amino acid sequence represented by SEQ ID NO: 1, 3 or 5, by using a gene recombination technique to introduce amino acid mutation(s).

Each of the polypeptides of (A) to (C) has hydrolysis activity (β-xylosidase activity) against a PNPX substrate at least under conditions of 80° C. and pH 4.0. As a result, a thermostable β-xylosidase can be obtained by having any of the polypeptides of (A) to (C) as the β-xylosidase catalytic domain.

The thermostable β-xylosidase according to the present invention uses PNPX as a substrate. The thermostable β-xylosidase may also use other β-glucans or oligosaccharides or the like besides PNPX as a substrate. Examples of substrates besides PNPX that can act as substrates for the thermostable β-xylosidase according to the present invention include PNPG, p-nitrophenyl-α-L-arabinofuranoside, p-nitrophenyl-α-L-arabinopyranoside, p-nitrophenyl-β-L-arabinopyranoside, p-nitrophenyl-β-D-mannopyranoside, p-nitrophenyl-α-D-galactopyranoside, p-nitrophenyl-β-D-galactopyranoside, glucans composed of β-1,3 and β-1,4 linkages such as lichenan, crystalline celluloses such as Avicel, crystalline bacterial cellulose (bacterial microcrystalline cellulose, BMCC) and filter paper, the non-crystalline cellulose known as phosphoric acid swollen Avicel (PSA), CMC, glucans composed of β-1,4 linkages, oligosaccharides composed of β-1,4 linkages such as cellobiose, glucans composed of β-1,3 and β-1,6 linkages such as laminarin, glucans composed of β-1,3 linkages, glucans composed of β-1,6 linkages, and oligosaccharides composed of β-1,6 linkages such as gentiobiose. In addition to PNPX, the thermostable β-xylosidase according to the present invention preferably also acts against at least one substrate selected from the group consisting of PNPG, p-nitrophenyl- α-L-arabinofuranoside, p-nitrophenyl-α-L-arabinopyranoside, p-nitrophenyl-β-L-arabinopyranoside, p-nitrophenyl-β-D-mannopyranoside, p-nitrophenyl-α-D-galactopyranoside and p-nitrophenyl-β-D-galactopyranoside, and more preferably also acts against PNPG as a substrate.

The thermostable β-xylosidase according to the present invention exhibits hydrolysis activity (β-xylosidase activity) against a PNPX substrate at least under conditions of pH 4.0, and preferably within a temperature range from 70 to 85° C., more preferably within a temperature range from 60 to 85° C., and still more preferably within a temperature range from 30 to 90° C. The optimum temperature of the thermostable β-xylosidase according to the present invention is preferably within a range from 70 to 85° C., and more preferably within a range from 75 to 85° C.

The optimum pH of the thermostable β-xylosidase according to the present invention varies depending on the reaction temperature, but falls within a range from pH 4.0 to 6.0. The thermostable β-xylosidase according to the present invention preferably exhibits β-xylosidase activity at least within a range from pH 4.0 to 8.0.

The thermostable β-xylosidase according to the present invention may also have other glycoside hydrolase activity besides the β-xylosidase activity. Examples of this other glycoside hydrolase activity include endoglucanase activity, xylanase activity, β-glucosidase activity and cellobiohydrolase activity. The thermostable β-xylosidase according to the present invention preferably has β-glucosidase activity in addition to the β-xylosidase activity.

The thermostable β-xylosidase according to the present invention may be an enzyme composed solely of the β-xylosidase catalytic domain including any of the aforementioned polypeptides of (A) to (C), or may also include other domains. Examples of these other domains include other domains of conventionally known β-xylosidases besides the enzyme catalytic domain. For example, the thermostable β-xylosidase according to the present invention also includes enzymes obtained by substituting the enzyme catalytic domain in a publicly known β-xylosidase with any of the aforementioned polypeptides of (A) to (C).

When the thermostable β-xylosidase according to the present invention includes one or more other domains besides the β-xylosidase catalytic domain in addition to the β-xylosidase catalytic domain, the thermostable β-xylosidase preferably includes a Fibronectin type III domain.

The Fibronectin type III domain may be positioned upstream (on the N-terminal side) or downstream (on the C-terminal side) from the β-xylosidase catalytic domain. Further, the Fibronectin type III domain and the β-xylosidase catalytic domain may be bonded either directly or via a linker region of appropriate length. In the thermostable β-xylosidase according to the present invention, a Fibronectin type III domain preferably exists either upstream or downstream from the β-xylosidase catalytic domain with a linker region positioned therebetween, and a thermostable β-xylosidase in which a Fibronectin type III domain exists downstream from the β-xylosidase catalytic domain with a linker region positioned therebetween is particularly preferred.

The thermostable β-xylosidase according to the present invention may also have, at either the N-terminal or the C-terminal, a signal peptide capable of migration to and localization within a specific region within a cell, or a signal peptide that causes secretion from a cell. Examples of these signal peptides include an apoplastic transport signal peptide, an endoplasmic reticulum retention signal peptide, a nuclear transport signal peptide, or a secretory signal peptide. Specific examples of the endoplasmic reticulum retention signal peptide include signal peptides including an HDEL amino acid sequence. In those cases when the thermostable β-xylosidase according to the present invention has a signal peptide at the N-terminal or the C-terminal, the thermostable β-xylosidase expressed in a transformant can be secreted from the cell or localized within the endoplasmic reticulum or the like of the cells.

Furthermore, the thermostable β-xylosidase according to the present invention may also have various types of tags added, for example at the N-terminal or the C-terminal of the thermostable β-xylosidase, so as to facilitate easy purification in the case of generation using an expression system. Examples of tags that may be used include the types of tags widely used in the expression or purification of recombinant proteins, such as an His tag, an HA (hemagglutinin) tag, an Myc tag and a Flag tag.

[Polynucleotide Encoding Thermostable β-Xylosidase]

The polynucleotide according to the present invention encodes the thermostable β-xylosidase according to the present invention. The thermostable β-xylosidase can be generated by using the expression system of a host made by introducing an expression vector incorporating the polynucleotide into the host.

Specifically, the polynucleotide according to the present invention is a polynucleotide having a region encoding a β-xylosidase catalytic domain, the region including any of the following nucleotide sequences (a) to (e):

(a) a nucleotide sequence encoding a polypeptide including the amino acid sequence represented by SEQ ID NO: 1, 3 or 5, (b) a nucleotide sequence encoding a polypeptide which includes an amino acid sequence in which at least one amino acid has been deleted, substituted, or added in the amino acid sequence represented by SEQ ID NO: 1,3 or 5, and has hydrolysis activity against a substrate of PNPX at least under conditions of 80° C. and pH 4.0, (c) a nucleotide sequence encoding a polypeptide which includes an amino acid sequence having 80% or greater sequence identity with the amino acid sequence represented by SEQ ID NO: 1, 3 or 5, and has hydrolysis activity against a substrate of PNPX at least under conditions of 80° C. and pH 4.0, (d) a nucleotide sequence, having 80% or greater sequence identity with a nucleotide sequence represented by SEQ ID NO: 2, 4 or 6, and encoding a polypeptide that has hydrolysis activity against a substrate of PNPX at least under conditions of 80° C. and pH 4.0, or (e) a nucleotide sequence of a polynucleotide which hybridizes with a polynucleotide including the nucleotide sequence represented by SEQ ID NO: 2, 4 or 6 under stringent conditions, the nucleotide sequence encoding a polypeptide having hydrolysis activity against a substrate of PNPX at least under conditions of 80° C. and pH 4.0.

In the present description, a "polynucleotide in which a nucleotide is deleted" means a polynucleotide in which a portion of the nucleotides which constitute the polynucleotide is missing (removed).

In the present description, a "polynucleotide in which a nucleotide is substituted" means a polynucleotide in which a nucleotide which constitutes the polynucleotide has been replaced with a different nucleotide.

In the present description, a "polynucleotide in which a nucleotide is added" means a polynucleotide in which a new nucleotide has been inserted within the polynucleotide.

In the present description, the expression "stringent conditions" can be exemplified by the method disclosed in Molecular Cloning: A Laboratory Manual, Third Edition (Sambrook et al., Cold Spring Harbor Laboratory Press). This example includes conditions in which hybridization is performed by incubation in a hybridization buffer composed of 6×SSC (composition of 20×SSC: 3 M sodium chloride, 0.3 M citric acid solution, pH 7.0), 5×Denhardt's solution (composition of 100×Denhardt's solution: 2% by mass of bovine serum albumin, 2% by mass of Ficoll, 2% by mass of polyvinylpyrrolidone), 0.5% by mass of SDS, 0.1 mg/mL of salmon sperm DNA, and 50% formamide, at a temperature of 42 to 70° C. for several hours to overnight. The washing buffer used in the washing performed after the incubation is preferably 1×SSC solution containing 0.1% by mass of SDS, and is more preferably 0.1×SSC solution containing 0.1% by mass of SDS.

In the aforementioned nucleotide sequences of (a) to (e), it is preferable to select a degenerate codon having a high frequency of usage in the host. For example, the aforementioned nucleotide sequence of (a) may be either the nucleotide sequence represented by SEQ ID NO: 2, 4 or 6, or a nucleotide sequence obtained by modifying the nucleotide sequence represented by SEQ ID NO: 2, 4 or 6 to codons having a higher frequency of usage in the host without changing the amino acid sequence encoded by the nucleotide sequence. This modification of codons can be achieved using a known gene sequence variation technique or artificial gene synthesis.

The polynucleotide including the nucleotide sequence represented by SEQ ID NO: 2, 4 or 6 may be chemically synthesized based on the nucleotide sequence information, or may be obtained from the natural world by using gene recombination techniques as either a full length gene that encodes AR19M-311-2 (also referred to as the "AR19M-311-2 gene" or the "gene clone AR19M-311-2") or a partial region thereof including the β-xylosidase catalytic domain (for example, a region encoding the partial region including the 325 amino acid residues from the threonine (T) at position 18 through to the alanine (A) at position 342 in SEQ ID NO: 3, a region encoding the partial region including the 236 amino acid residues from the isoleucine (I) at position 381 through to the threonine (T) at position 616 in SEQ ID NO: 3, or a region encoding the partial region including the 599 amino acid residues from the threonine (T) at position 18 through to the threonine (T) at position 616 in SEQ ID NO: 3). The full length of the AR19M-311-2 gene or the partial region thereof can be obtained, for example, by collecting a sample containing microorganisms from the natural world, and conducting PCR using a genomic DNA recovered from the sample as a template, with a forward primer and a reverse primer designed by normal methods based on the nucleotide sequence represented by SEQ ID NO: 2, 4 or 6. The cDNA synthesized by a reverse transcription reaction using mRNA recovered from the sample as a template may also be used as a template. The sample from which the nucleic acid for use as a template is recovered is preferably a sample collected from a high-temperature environment such as hot spring soil.

In the aforementioned nucleotide sequence of (d), the sequence identity with the nucleotide sequence represented by SEQ ID NO: 2, 4 or 6 is not specifically limited as long as it is 80% or greater but less than 100%, but the sequence identity is preferably 85% or greater but less than 100%, more preferably 90% or greater but less than 100%, and still more preferably 95% or greater but less than 100%.

The sequence identity (homology) between a pair of nucleotide sequences is determined by juxtaposing the two nucleotide sequences, while inserting gaps in some parts of the sequences to account for insertions and deletions, so as to achieve the best match between corresponding nucleotides, and then calculating the proportion of matched nucleotides relative to the whole nucleotide sequences, excluding gaps, in the resulting alignment. The sequence identity between a pair of nucleotide sequences can be determined using a variety of homology search software well known in the art. The sequence identity value between nucleotide sequences in the present invention is obtained by calculation on the basis of an alignment obtained from the publicly known homology search software BLASTN.

For example, each of the polynucleotides including the aforementioned nucleotide sequence of (b), (c) or (d) can be artificially synthesized by deleting, substituting, or adding one or a plurality of nucleotides in a polynucleotide including the nucleotide sequence represented by SEQ ID NO: 2, 4 or 6. Further, the nucleotide sequence of (b), (c) or (d) may also be a full length sequence of a homologous gene of the AR19M-311-2 gene or a partial sequence thereof. The homologous gene of the AR19M-311-2 gene can be obtained by a gene recombination technique used in obtaining homologous genes of a gene for which the nucleotide sequence is already known.

The polynucleotide according to the present invention may have only the region encoding the β-xylosidase catalytic domain, or may also have, in addition to this region, one or more other regions encoding a cellulose-binding module, a linker sequence, various types of signal peptides, or various types of tags or the like.

[Expression Vector]

The expression vector according to the present invention incorporates the aforementioned polynucleotide according to the present invention, and is capable of expressing, in a host cell, a polypeptide having hydrolysis activity against a PNPX substrate at least under conditions of 80° C. and pH 4.0. In other words, the expression vector of the present invention is an expression vector into which the polynucleotide according to the present invention has been incorporated in a state capable of expressing the thermostable β-xylosidase according to the present invention. More specifically, it is necessary that an expression cassette, composed, in order from the upstream side, of DNA having a promoter sequence, the aforementioned polynucleotide according to the present invention and DNA having a terminator sequence, is incorporated into the expression vector. Incorporation of the polynucleotide into an expression vector can be achieved using known gene recombination techniques. A commercially available expression vector preparation kit may also be used to achieve incorporation of the polynucleotide into the expression vector.

In the present description, an "expression vector" is a vector including, in order from the upstream side, DNA having a promoter sequence, DNA having a sequence for incorporating foreign DNA, and DNA having a terminator sequence.

The aforementioned expression vector may be a vector for introduction into a prokaryotic cell such as *E. coli*, or a vector for introduction into a eukaryotic cell such as a yeast, a filamentous fungus, an insect cultured cell, a mammalian cultured cell, or a plant cell. Any arbitrary widely used expression vector can be selected and used in accordance with the respective host.

The expression vector according to the present invention is preferably an expression vector into which not only the aforementioned polynucleotide according to the present invention, but also a drug resistance gene or the like, has been incorporated. This facilitates the screening of host cells transformed by the expression vector and non-transformed host cells.

Examples of the drug resistance gene include a kanamycin resistance gene, a hygromycin resistance gene and a bialaphos resistance gene.

[Transformant]

The transformant according to the present invention is a transformant into which the expression vector according to the present invention has been introduced. In this transformant, the aforementioned thermostable β-xylosidase according to the present invention can be expressed. The host into which the expression vector is introduced may be a prokaryotic cell such as E. coli, or a eukaryotic cell such as a yeast, a filamentous fungus, an insect cultured cell, a mammalian cultured cell, or a plant cell. In other words, examples of the transformant according to the present invention include E. coli, a yeast, a filamentous fungus, an insect cultured cell, a mammalian cultured cell or a plant cell into which the expression vector according to the present invention has been introduced.

By culturing a transformant of E. coli, the thermostable β-xylosidase according to the present invention can be generated more easily and in large amounts. On the other hand, because proteins are glycosylated in eukaryotic cells, by using a transformant of a eukaryotic cell, a thermostable β-xylosidase can be generated which exhibits superior thermostability to that achieved by using a transformant of a prokaryotic cell.

There are no particular limitations on the method used for producing the transformant using the expression vector, and the types of methods typically used in the production of transformants can be employed. Examples of methods that can be used include a heat shock method, an Agrobacterium method, a particle gun method, an electroporation method, and a PEG (polyethylene glycol) method. Of these, if the host is a plant cell, a particle gun method or an Agrobacterium method is preferred.

When a prokaryotic cell, a yeast, a filamentous fungus, an insect cultured cell, or a mammalian cultured cell or the like is used as the host, the obtained transformant can generally be cultured by a conventional method in a similar manner to that of the non-transformed host.

[Method for Producing Thermostable β-Xylosidase]

The method for producing a thermostable β-xylosidase according to the present invention is a method for generating a thermostable β-xylosidase in the aforementioned transformant according to the present invention. By culturing a transformant that has been produced using an expression vector into which the aforementioned polynucleotide according to the present invention has been incorporated downstream from a promoter having no ability to regulate the timing or the like of the expression, the thermostable β-xylosidase according to the present invention is expressed constitutively within the transformant. On the other hand, in the case of a transformant produced using a so-called expression inducible promoter to induce the expression by means of a specific compound or temperature condition or the like, the thermostable β-xylosidase is expressed in the transformant by culturing the transformant and conducting an induction treatment suitable for the respective expression-inducing condition.

The thermostable β-xylosidase generated by the transformant may be used in a state where it is retained inside the transformant, or may be extracted from the transformant and purified.

The method used for extracting and purifying the thermostable β-xylosidase from the transformant is not particularly limited, as long as the method does not impair the activity of the thermostable β-xylosidase, and extraction can be carried out by methods commonly used for extracting polypeptides from cells or biological tissue. Examples of the method include a method in which the transformant is immersed in an appropriate extraction buffer to extract the thermostable β-xylosidase, and the resulting liquid extract and the solid residue are then separated. The extraction buffer preferably contains a solubilizing agent such as a surfactant. If the transformant is a plant, then the transformant may be shredded or crushed prior to immersion in the extraction buffer.

Further, in terms of the method used for separating the liquid extract and the solid residue, known solid-liquid separation treatments such as a filtration method, pressurized filtration method or centrifugation treatment may be used, or the extraction buffer containing the immersed transformant may be squeezed. The thermostable β-xylosidase in the liquid extract can be purified by known purification methods such as a salting-out method, ultrafiltration method, or chromatography method.

If the thermostable β-xylosidase according to the present invention is expressed in a state having a secretory signal peptide in the transformant, then a solution containing the thermostable β-xylosidase can be readily obtained by culturing the transformant and then collecting the culture liquid supernatant obtained by removal of the transformant from the obtained culture. Further, if the thermostable β-xylosidase according to the present invention has a tag such as a His tag, then the thermostable β-xylosidase in the liquid extract or in the culture supernatant can be easily purified by an affinity chromatography method using the tag.

In other words, the method for producing a thermostable β-xylosidase according to the present invention includes culturing the transformant according to the present invention, generating the thermostable β-xylosidase within the transformant, and, according to need, extracting the thermostable β-xylosidase from the transformant and purifying the thermostable β-xylosidase.

[Glycoside Hydrolase Mixture]

The glycoside hydrolase mixture according to the present invention includes the aforementioned thermostable β-xylosidase according to the present invention or a thermostable β-xylosidase produced by the method for producing a thermostable β-xylosidase according to the present invention, and at least one other glycoside hydrolase. The thermostable β-xylosidase produced by the aforementioned method for producing a thermostable β-xylosidase according to the present invention may be in a state where it is incorporated inside the transformant, or may be extracted from the transformant and purified. By using the thermostable β-xylosidase according to the present invention as a mixture with one or more other glycoside hydrolases in a polysaccharide hydrolysis reaction, materials composed of persistent lignocellulose can be degraded more efficiently.

There are no particular limitations on the other glycoside hydrolase besides the aforementioned thermostable β-xylosidase included in the glycoside hydrolase mixture, as long as it exhibits lignocellulose hydrolysis activity. Examples of the other glycoside hydrolase besides the aforementioned thermostable β-xylosidase included in the glycoside hydrolase mixture include hemicellulases such as xylanases, as well as cellobiohydrolases, β-glucosidases and endoglucanases. The glycoside hydrolase mixture according to the present invention is preferably a mixture containing at least one of a hemicellulase and an endoglucanase in addition to the aforementioned thermostable β-xylosidase, and is more preferably a mixture containing both a hemicellulase and an endoglucanase in addition to the aforementioned thermostable β-xylosidase. Among the various possibilities, the glycoside hydrolase mixture according to the present invention is preferably a mixture containing at least one glycoside hydrolase selected from the group consisting of xylanases, β-xylosidases, cellobiohydrolases and endoglucanases in addition to the aforementioned thermostable β-xylosidase, and is more preferably a mixture containing all of a xylanase, a β-xylosidase, a cellobiohydrolase and an endoglucanase in addition to the thermostable β-xylosidase.

The other glycoside hydrolase included in the glycoside hydrolase mixture besides the aforementioned thermostable β-xylosidase is preferably a thermostable glycoside hydrolase having glycoside hydrolase activity at least at 85° C., and is more preferably a thermostable glycoside hydrolase having glycoside hydrolase activity at 70 to 90° C. By ensuring that all of the enzymes contained in the glycoside hydrolase mixture are thermostable (that is, have an optimum temperature for the enzymatic activity or a melting temperature for the enzyme protein of 70° C. or higher), the degradation reaction of materials containing lignocellulose by the glycoside hydrolase mixture can be conducted efficiently under high-temperature conditions. In other words, if the glycoside hydrolase mixture contains only thermostable glycoside hydrolases, then by using the glycoside hydrolase mixture in a hydrolysis treatment of a material containing lignocellulose, it becomes possible to conduct a lignocellulose hydrolysis reaction in a high-temperature environment in which the hydrolysis temperature is from 70 to 90° C. With this high-temperature hydrolysis, the amount of enzymes and the time required for the hydrolysis can be reduced markedly, and the hydrolysis costs can be cut dramatically.

[Method for Producing Lignocellulose Degradation Product]

The method for producing a lignocellulose degradation product according to the present invention is a method for obtaining a lignocellulose degradation product which includes hydrolyzing either oligosaccharides generated from hemicellulose by a xylanase or oligosaccharides generated from cellulose by a cellobiohydrolase with the thermostable β-xylosidase according to the present invention, thereby producing monosaccharides.

Here, the expression "lignocellulose degradation product" means a product generated by breaking the β-xylosidic bonds or β-glycosidic bonds in a material composed of lignocellulose, such as a lignocellulose-containing material containing hemicellulose or cellulose, and preferably a material containing oligosaccharides having β-xylosidic bonds or oligosaccharides having β-glycosidic bonds. Specific examples include monosaccharide such as glucose, xylose and the like.

More specifically, a hemicellulose or cellulose degradation product, and specifically a product generated by breaking β-xylosidic bonds or β-glycosidic bonds, is generated by bringing a material containing lignocellulose, such as a lignocellulose-containing material containing hemicellulose or cellulose, and preferably a material containing oligosaccharides having β-xylosidic bonds or oligosaccharides having β-glycosidic bonds, into contact with the thermostable β-xylosidase according to the present invention, the transformant according to the present invention, a thermostable β-xylosidase produced by the method for producing a thermostable β-xylosidase according to the present invention, or the glycoside hydrolase mixture according to the present invention.

Another aspect of the method for producing a lignocellulose degradation product according to the present invention is a method for generating a product (for example, monosaccharide such as glucose, xylose and the like) mainly by breaking the β-xyloside binding sites of hemicellulose, and preferably oligosaccharides having β-xylosidic bonds, or by breaking the β-glycoside binding sites of cellulose, and preferably oligosaccharides having β-glycosidic bonds, by bringing a material containing lignocellulose, such as a lignocellulose-containing material containing hemicellulose or cellulose, and preferably a material containing oligosaccharides having β-xylosidic bonds or oligosaccharides having β-glycosidic bonds, into contact with the thermostable β-xylosidase according to the present invention, the transformant according to the present invention, or a thermostable β-xylosidase produced by the method for producing a thermostable β-xylosidase according to the present invention.

Yet another aspect of the method for producing a lignocellulose degradation product according to the present invention is a method for generating a product (for example, monosaccharide such as glucose, xylose and the like) by breaking the β-glycoside binding sites of hemicellulose or cellulose, by bringing a material containing lignocellulose, such as a lignocellulose-containing material containing hemicellulose or cellulose, into contact with the glycoside hydrolase mixture according to the present invention.

There are no particular limitations on the material composed of lignocellulose such as a lignocellulose-containing material containing hemicellulose or cellulose, and preferably a material containing oligosaccharides having β-xylosidic bonds or oligosaccharides having β-glycosidic bonds, provided that the material contains hemicellulose or cellulose, or preferably oligosaccharides having β-xylosidic bonds or oligosaccharides having β-glycosidic bonds. Specific examples of such materials include cellulosic biomass such as weeds and agricultural waste materials, or used paper or the like. The material is preferably subjected to a mechanical treatment such as crushing or shredding, a chemical treatment with acid or alkali or the like, or a treatment such as immersion or dissolution in an appropriate buffer, prior to being brought into contact with the thermostable β-xylosidase according to the present invention.

In other words, the method for producing a lignocellulose degradation product according to the present invention may also include a step in which the aforementioned material is treated mechanically, treated chemically, or treated by immersion or dissolution in a buffer, prior to being brought into contact with the thermostable β-xylosidase according to the present invention.

The reaction conditions for the hydrolysis reaction of the material composed of lignocellulose by the thermostable β-xylosidase according to the present invention may be any conditions under which the thermostable β-xylosidase exhibits cellooligosaccharide hydrolysis activity. For example, the reaction is preferably conducted at a temperature of 60 to 90° C. and a pH of 5.0 to 9.0, more preferably conducted at a temperature of 70 to 90° C. and a pH of 5.0 to 9.0, and still more preferably conducted at a temperature of 70 to 90° C. and a pH of 6.0 to 8.5. The reaction time for the hydrolysis reaction may be adjusted appropriately with due consideration of the type, the method of pretreatment, and the amount and the like of the material supplied to the hydrolysis reaction. For example, the hydrolysis reaction may be performed for a reaction time of 10 minutes to 100 hours, but in the case of degradation of a cellulosic biomass, the hydrolysis reaction time is preferably from 1 to 100 hours.

In the hydrolysis reaction of the material composed of lignocellulose, it is also preferable to use at least one other type of glycoside hydrolase in addition to the thermostable β-xylosidase according to the present invention, with the enzymes used either simultaneously or separately. This other glycoside hydrolase may be similar to the glycoside hydrolases mentioned above for inclusion in the aforementioned glycoside hydrolase mixture, and is preferably a thermostable glycoside hydrolase having glycoside hydrolase activity at least at 85° C., and preferably at least at temperatures of 70 to 90° C. Further, one aspect of the aforementioned method for producing a lignocellulose degradation product uses the thermostable β-xylosidase according to the present invention, the transformant according to the present invention, or a thermostable β-xylosidase produced by the method for producing a thermostable β-xylosidase according to the present invention, whereas another aspect of the method uses the aforementioned glycoside hydrolase mixture.

EXAMPLES

Next, the present invention is described in further detail based on a series of Examples, but the present invention is in no way limited by the following Examples.

Example 1

Cloning of Novel Thermostable β-Xylosidase from Hot Spring Soil

<1> DNA Extraction from Hot Spring Soil and Whole Genome Sequencing (WGS)

With the purpose of searching for genes of novel thermostable β-xylosidases which exhibit activity at 70 to 90° C., soil DNA was collected from neutral to weakly alkaline hot springs, and nucleotide sequencing was conducted of the metagenomic DNA of the microbial flora contained in the soils.

The soil samples from neutral to weakly alkaline hot springs were obtained by collecting hot spring water containing soil, clay and biomat from five sampling points (metagenomic DNA samples N2, AR19, AR15, OJ1 and H1) at 3 locations in Japan having gushing high-temperature outdoor hot springs. These hot spring soil samples each had a temperature within a range from 58 to 78° C. and a pH within a range from 7.2 to 8 at the time of collection.

DNA was extracted from 10 g of each of the collected hot spring soil samples by using a DNA extraction kit (ISOIL Large for Beads ver.2, manufactured by NIPPON GENE Co., Ltd.). The extracted DNA was subjected to shotgun sequencing of the metagenomic DNA using a sequencer GS FLX Titanium 454 manufactured by Roche Diagnostics Ltd., and a sequencer HiSeq 2000 manufactured by Illumina, Inc. Five μg of the extracted DNA was used in the 454 sequencer, whereas in the HiSeq 2000 sequencer, an amplified product prepared using a genome DNA amplification kit (GenomiPhi V2 DNA Amplification Kit, manufactured by GE Healthcare, Inc.) was used to perform the metagenomic DNA sequencing. In the case of sequencing using the HiSeq 2000, the DNA library and the reagent were introduced into the flow cell using a cBot manufactured by Illumina, Inc., and from a single DNA molecule, a cluster having the same sequence was formed automatically within the flow cell. Using the HiSeq 2000, 101 bp paired end sequencing was performed, thus obtaining the metagenomic sequence data.

Metagenomic DNA sequencing of the hot spring soil sample AR19 in the 454 sequencer yielded an average read length of 396 bp, a total read number of 2,766,332, and a total quantity of sequenced genomes of 1,106,243,280 bp, and sequencing in the HiSeq 2000 sequencer yielded an average read length of 92.65 bp paired ends, a total read number of 894,238,096, and a total quantity of sequenced genomes of 83,112,168,755 bp, meaning a whole genome sequence (WGS) data set totaling 84.2 Gbp was obtained.

<2> Assembly and Statistics of Hot Spring Metagenomic Data

For the nucleotide sequences read by the 454 sequencer and the HiSeq 2000 sequencer, CLC Genomics Workbench (ver. 5.5.1) from CLC bio A/S was used to perform quality filtering and de novo assembly. Following quality filtering, the total read length of the reads obtained from the 454 sequencer was 2,766,328 bp, and the total read length of the nucleotide sequence data obtained from the HiSeq 2000 sequencer was 81,323,692,563 bp. Following assembly, the number of contigs having a length of 500 bp or longer was 967,925, the total length was 419,787,603 bp, and the maximum contig length was 287,641 bp.

<3> Prediction of Open Reading Frames (ORFs) of β-Xylosidase

Sequences having EC numbers of 3.2.1.4 (cellulase), 3.2.1.21 (β-glucosidase), 3.2.1.37 (β-xylosidase), 3.2.1.91 (cellulose 1,4-β-cellobiosidase) and 3.2.1.8 (endo-1,4-β-xylanase) were downloaded (date of access: Dec. 9, 2011) from the UniProt database, and a proteome local database of these glycoside hydrolase genes was constructed. Using the annotation software Metagene (Noguchi et al., DNA Research, 2008, 15(6)), gene regions (=open reading frames) were predicted from the contig sequences obtained in section <2> above (Metagene option: -m). In order to extract the glycoside hydrolase gene from the predicted ORFs, reference was made to the local database using BLASTP (blastall ver. 2.2.18). The optional conditions for BLASTP were set such that: "Filter query sequence=false", "Expectation value (E)<1e$^{-20}$" (hereafter, default values were set such that: "Cost to open a gap=−1", "Cost to extended gap=−1", "X dropoff value for gapped alignment=0", "Threshold for extending hits=0", and "Word size=default"), and the hit ORF sequences were collected as glycoside hydrolase genes. The collected nucleotide sequences included nucleotide sequences of various glycoside hydrolase genes such as cellulases, endohemicellulases and debranching enzymes.

<4> Glycoside Hydrolase (GH) Family Classification of Genes

Functional classification of the nucleotide sequences collected in section <3> above was performed with reference to the protein functional domain sequence database Pfam HMMs (Pfam version 23.0 and HMMER v2.3; Finn et al., Nucleic Acids Research Database, 2010, Issue 38, pp. D211-222). Specifically, the glycoside hydrolase (GH) family of each of the nucleotide sequences collected in section <3> above was determined on the basis of homology with the Pfam domain database by using the protein motif search program HMMER (Durbin et al., "The theory behind profile HMMs. Biological sequence analysis: probabilistic models of proteins and nucleic acids", 1998, Cambridge University Press; hmmpfam (Ver. 2.3.2), E-value cutoff<1e$^{-5}$;

Database=Pfam_fs (models that can be used to find fragments of the represented domains in a sequence)). Nucleotide sequences which covered 70% or more of the GH catalytic domain sequence were counted as enzyme genes belonging to that particular family.

From the metagenome AR19 sequence data of length 84.2 Gbp, 602,589 ORFs were predicted by the Metagene software, and the number of full-length ORFs was 251,146.

Based on the BLASTP homology search, 406 ORF hits were obtained for β-glucosidase or β-xylosidase sequences. Among these 406 ORFs, 168 ORFs were predicted as β-glucosidase genes or β-xylosidase genes using Pfam HMMs, whereas the remaining 238 ORFs (of which 92 were full-length ORFs and 146 were partial length ORFs) either exhibited a coverage of the GH catalytic domain sequence of less than 70%, or produced no hits in the Pfam database.

The GH family classification results of the 168 ORFs that were predicted as β-glucosidase genes or β-xylosidase genes are shown in Table 1. Sequences for which the coverage of the GH catalytic domain sequence was less than 70%, and sequences for which ho homology could be confirmed in Pfam were classified as GH unknown. As shown in Table 1, among the ORFs predicted as β-glucosidase or β-xylosidase from the AR19 metagenome, 19 full-length ORFs belonging to the GH1 family, 57 full-length ORFs belonging to the GH3 family, 13 full-length ORFs belonging to the GH31 family, and 13 full-length ORFs belonging to the GH43 family were obtained. Primers were designed for all of the full-length ORFs that were predicted as β-glucosidase genes or β-xylosidase genes, and the genes were cloned from the hot spring soil metagenomic DNA by PCR. As a result, a β-xylosidase gene was isolated from the open reading frame AR19M-311 belonging to the GH 3 family and having a xylosidase nucleotide sequence.

TABLE 1

| AR19 Metagenome | GH family classification of β-glucosidase genes or β-xylosidase genes | | | | | |
|---|---|---|---|---|---|---|
| | GH1 | GH3 | GH31 | GH43 | other GHs | Total |
| full-length ORFs | 19 | 57 | 13 | 13 | 3 | 105 |
| partial length ORFs | 3 | 52 | 4 | 4 | 0 | 63 |
| Total number of ORFs | 22 | 109 | 17 | 17 | 3 | 168 |

<5> Open Reading Frame AR19M-311

The open reading frame AR19M-311 encoded a polypeptide including 751 amino acid residues (SEQ ID NO: 1) starting with a methionine as the amino acid residue at position 1, and was a full-length sequence (SEQ ID NO: 2) in which the 3' terminal of the nucleotide sequence encoding the polypeptide ended with a termination codon. Based on the sequence homology of the motif, it was predicted that the protein was a multi-domain protein in which the 325 amino acid residues from the threonine (T) at position 18 through to the alanine (A) at position 342 in the polypeptide encoded by the open reading frame AR19M-311 represented a catalytic domain of glycoside hydrolase family 3, the 236 amino acid residues from the isoleucine (I) at position 381 through to the threonine (T) at position 616 represented a catalytic domain of glycoside hydrolase family 3, and the 70 amino acid residues from the glutamic acid (E) at position 651 through to the serine (S) at position 720 represented a Fibronectin type III domain. According to analysis using the signal sequence prediction software SignalP 4.1, the amino acid sequence from the methionine (M) at position 1 that represents the start codon through to position 17 does not encode any secretion signal, and its function was unclear.

<6> Gene Cloning

Using a forward primer composed of the nucleotide sequence represented by SEQ ID NO: 9 (5'-CACCATG-GAAGAAAGATGGTTACAAAG-3': 4 nucleotides (CACC) were added to the 5'-end of the nucleotide sequence represented by SEQ ID NO: 7, wherein the CACC added to the 5' side is a sequence to enable insertion into a vector), and a reverse primer composed of the nucleotide sequence represented by SEQ ID NO: 8 (5'-TTAAGGTTCTATAAT-TACCTCGCTAG-3'), PCR was performed using the hot spring soil DNA that had been amplified by the genome DNA amplification kit (GenomiPhi V2 DNA Amplification Kit, manufactured by GE Healthcare, Inc.) as a template. The nucleotide sequence represented by SEQ ID NO: 7 is homologous (identical) with the partial sequence composed of the nucleotides from positions 1 to 23 of the nucleotide sequence represented by SEQ ID NO: 2, 4 or 6. Further, the nucleotide sequence represented by SEQ ID NO: 8 is complementary with the partial sequence composed of the nucleotides from positions 2,231 to 2,256 of the nucleotide sequence represented by SEQ ID NO: 2, 4 or 6. The amplified PCR product was inserted into a pET101/D-TOPO vector of a Champion pET Directional TOPO Expression Kit (manufactured by Life Technologies Inc.), and transformed into a One Shot TOP10 strain. Positive clones were selected by colony PCR and cultured in an LB liquid medium containing 100 mg/L of ampicillin at a temperature of 37° C. and 200 rpm for 17 to 20 hours, and then plasmids were prepared using a miniprep kit (Wizard plus SV Minipreps DNA Purification System, manufactured by Promega Corporation). Sequence confirmation of the prepared plasmids was performed using sequencer (3730 DNA Analyzer, manufactured by Life Technologies Corporation).

Two gene clones AR19M-311-2 and AR19M-311-11 were obtained from the open reading frame AR19M-311 bp PCR cloning. The nucleotide sequence (SEQ ID NO: 4) of the β-xylosidase candidate gene clone AR19M-311-2 (hereafter also referred to as the "AR19M-311-2 gene") and the nucleotide sequence (SEQ ID NO: 6) of the β-xylosidase candidate gene clone AR19M-311-11 (hereafter also referred to as the "AR19M-311-11 gene") each contained 2256 bp, the same number as the open reading frame AR19M-311 (SEQ ID NO: 2), but differed from the open reading frame AR19M-311 in 19 nucleotides and 20 nucleotides respectively. Table 2 lists the nucleotides where the AR19M-311-2 gene and the AR19M-311-11 gene differ from the open reading frame AR19M-311. The differences in the nucleotide sequences of the open reading frame AR19M-311 and the AR19M-311-2 and AR19M-311-11 genes are thought to be due to misassembly in the metagenomic shotgun sequencing or single nucleotide polymorphism of the genes.

TABLE 2

| Nucleotide No. | AR19M-311 | AR19M-311-2 | AR19M-311-11 |
|---|---|---|---|
| 438 | T | T | C |
| 560 | G | A | A |
| 561 | A | G | G |
| 564 | A | G | A |
| 567 | A | T | T |
| 570 | T | A | A |
| 579 | A | C | C |
| 581 | T | C | C |

TABLE 2-continued

| Nucleotide No. | AR19M-311 | AR19M-311-2 | AR19M-311-11 |
|---|---|---|---|
| 606 | T | A | A |
| 609 | T | G | G |
| 612 | G | A | A |
| 615 | A | T | T |
| 617 | C | G | G |
| 618 | A | T | T |
| 625 | T | C | C |
| 630 | T | C | C |
| 672 | C | C | A |
| 932 | C | T | T |
| 1064 | T | C | T |
| 1086 | T | T | C |
| 1107 | C | C | T |
| 1224 | T | C | C |
| 1903 | G | A | G |

The amino acid sequence (SEQ ID NO: 3) of the polypeptide (AR19M-311-2) encoded by the AR19M-311-2 gene and the amino acid sequence (SEQ ID NO: 5) of the polypeptide (AR19M-311-11) encoded by the AR19M-311-11 gene differ from the amino acid sequence (SEQ ID NO: 1) encoded by the open reading frame AR19M-311 in 6 amino acids and 4 amino acids respectively. Table 3 lists the amino acid residues where AR19M-311-2 and AR19M-311-11 differ from the protein encoded by the open reading frame AR19M-311. Moreover, FIG. 2 illustrates the sequence alignment of the amino acid residues of AR19M-311, AR19M-311-2, and AR19M-311-11. In this figure, "•" represents identical amino acid residues, whereas substituted amino acid residues are shown in white text on black. AR19M-311-2 and AR19M-311-11 differ at only two amino acid residues, with the alanine (A) at position 355 and the isoleucine (I) at position 635 of AR19M-311-2 both being valine (V) residues in AR19M-311-11.

TABLE 2

| Amino acid No. | AR19M-311 | AR19M-311-2 | AR19M-311-11 |
|---|---|---|---|
| 187 | R | K | K |
| 194 | V | A | A |
| 206 | A | G | G |
| 311 | T | I | I |
| 355 | V | A | V |
| 635 | V | I | V |

FIG. 1 shows the alignment of the amino acid sequence of the β-xylosidase catalytic domain of the gene clone AR19M-177-2 and the amino acid sequence of a β-xylosidase belonging to the GH3 family of *Dictyoglomus thermophilum*. In FIG. 1, the amino acids shown in white on black are the amino acid residues identical to both amino acid sequences, the amino acids shown in black on a shaded grey background indicate positions where the amino acid residues in the sequences are similar, and "–" indicates a gap in a sequence. Including gaps, AR19M-311-2 exhibited 70% sequence identity with the β-xylosidase belonging to the GH3 family of *Dictyoglomus thermophilum*.

<7> Gene Expression and Purification of β-Xylosidase Enzyme Protein

Following sequence confirmation, the plasmid having the target gene (the AR19M-311-2 gene or the AR19M-311-11 gene) was introduced into *E. coli* for protein expression using the heat shock method. The BL21 Star (DE3) strain provided in the Champion pET Directional TOPO Expression Kit (manufactured by Life Technologies Inc.) was used as the competent cell for the transformation. Expression of the target protein was induced by inoculating the *E. coli* having the target gene into an LB medium containing 100 mg/L of ampicillin, culturing to about $OD_{600}$=0.2 to 0.8, subsequently adding IPTG (isopropyl-β-D(–)-thiogalactopyranoside), and performing additional culturing for 5 to 20 hours. Following completion of the culturing, the *E. coli* was collected by centrifugation, and an amount of 50 mM Tris-HCl buffer (pH 8.0) equivalent to 1/10 of the volume of the culture liquid was then added and suspended. Subsequently, a process consisting of 5 minutes disrupting and then 5 minutes of rest was repeated 7 or 8 times using an ultrasonic disrupter Astrason 3000 (manufactured by MISONIX Inc.), thus obtaining a crude extract of the gene recombinant *E. coli* containing the target protein. This gene recombinant *E. coli* crude extract was filtered through a filter (pore size φ=0.45 μm, manufactured by EMD Millipore Corporation), and the resulting filtrate was used as a gene recombinant *E. coli* homogeneous supernatant.

The gene recombinant *E. coli* homogeneous supernatants of the AR19M-311-2 gene and the AR19M-311-11 gene were each loaded onto an ion exchange column HiTrap Q HP (manufactured by GE Healthcare, Inc.) equilibrated with 50 mM Tris-HCl buffer (pH 8.0), and a medium-high pressure liquid chromatography system AKTA design (manufactured by GE Healthcare, Inc.) was used to fractionate proteins with a concentration gradient of 0 to 50% in 50 mM Tris-HCl buffer (pH 8.0) containing 1 M of NaCl. The fractions exhibiting β-xylosidase activity were pooled, and a centrifugal ultrafiltration membrane VIVASPIN 20 (manufactured by Sartorius stedim Biotech SA) was used to exchange the buffer to a 50 mM Tris-HCl buffer (pH 8.0) containing 750 mM of ammonium sulfate. The fractions with β-xylosidase activity following the buffer exchange were loaded onto a hydrophobic interaction separation column HiTrap Phenyl HP (manufactured by GE Healthcare, Inc.) equilibrated with the same solution, and the proteins were fractionated with a concentration gradient of 0 to 100% in 50 mM Tris-HCl buffer (pH 8.0). The fractions exhibiting β-xylosidase activity were pooled and then concentrated using the VIVASPIN 20 until the liquid volume reached about 8 mL. The concentrated sample was loaded onto a gel filtration column Hiload 26/60 superdex 200 pg (manufactured by GE Healthcare, Inc.) equilibrated with 50 mM Tris-HCl buffer (pH 8.0) containing 150 mM of NaCl, and was fractionated by flowing the same buffer of 1 to 1.5 fold volume of the column volume at a flow rate of 2 to 3 mL/min.

Subsequently, in the case of AR19M-311-2, the fractions exhibiting xylosidase activity were pooled and subjected to a buffer exchange into 50 mM Tris-HCl buffer (pH 8.0) and concentrated using the VIVASPIN 20, and a HiTrap Q HP was then used to further fractionate the proteins in the same manner as described above. Subsequently, for both the AR19M-311-2 and the AR19M-311-11, the fractions exhibiting xylosidase activity were respectively pooled, subjected to a buffer exchange into 50 mM Tris-HCl buffer (pH 8.0) and then concentrated, thus yielding a purified enzyme having a final concentration of about 3.77 mg/mL in the case of AR19M-311-2, and a purified enzyme having a final concentration of about 35.6 mg/mL in the case of AR19M-311-11.

The gene recombinant *E. coli* homogenous supernatants and the purified enzymes were checked by SDS-PAGE (SDS-polyacrylamide gel electrophoresis) analysis. For each gene, 5 μg of the gene recombinant *E. coli* homogenous supernatant or 0.5 μg of the purified enzyme was mixed with a sample buffer 4-fold concentrate containing 2-mercaptoethanol (manufactured by Wako Pure Chemical Industries, Ltd.) to adjust the concentration to one-fold, and following treatment of the thus obtained sample at 95° C. for 4 minutes, electrophoresis was performed using a 10% Criterion TGX stain-free gel (manufactured by Bio-Rad Laboratories, Inc.). Following electrophoresis, the protein bands were visualized using an imaging system ChemiDoc (manufactured by Bio-Rad Laboratories, Inc.).

Figure 3B:
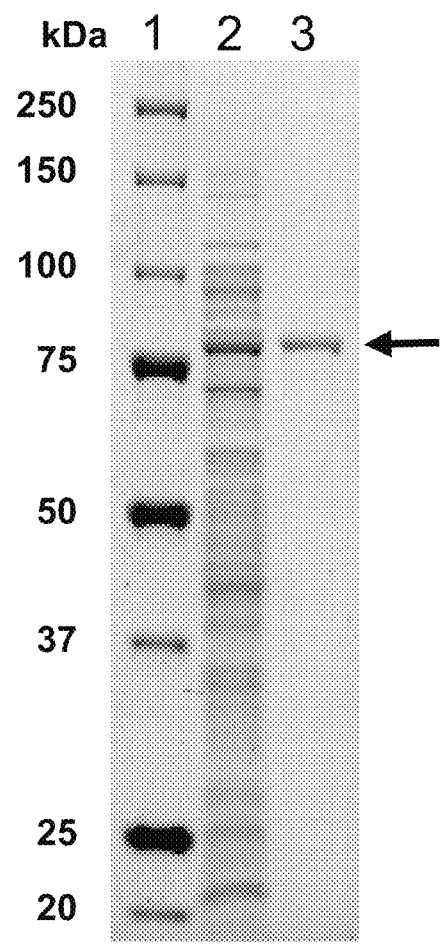
FIG. 3B is a diagram showing the SDS-PAGE analysis results in Example 1 of the AR19M-311-11 protein obtained by expressing the AR19M-311-11 gene in *E. coli*.

FIG. 3A or 3B shows the SDS-PAGE analysis results of the gene recombinant E. coli homogenous supernatants prepared from the transformed E. coli into which the AR19M-311-2 gene (FIG. 3A) or the AR19M-311-11 gene (FIG. 3B) had been introduced, and the purified enzymes produced from the gene recombinant E. coli homogenous supernatants. The figure shows electrophoretic patterns in which lane 1 represents a protein mass marker, lane 2 represents the gene recombinant E. coli homogenous supernatant, and lane 3 represents the purified enzyme. For both the AR19M-311-2 gene and the AR19M-311-11 gene, the results revealed a strong band in the gene recombinant E. coli homogenous supernatant (lane 2) near the mass expected from the amino acid sequence (SEQ ID NO: 3 or 5 respectively), and a single band corresponding with this band (indicated by an arrow in the figure) was observed in each of the purified enzymes (lane 3).

<8> Measurement of β-Xylosidase Activity Against PNPX Substrate (PNPX Hydrolysis Activity)

In order to compare the specific activities of the prepared AR19M-311-2 and AR19M-311-11, the PNPX hydrolysis activity (β-xylosidase activity) of each was investigated. For each enzyme, a purified enzyme solution prepared by diluting the purified enzyme obtained in section <7> above with water to obtain a concentration of 10 ng/μL was used.

PNPX was used as the substrate for measuring the β-xylosidase activity. A solution prepared by dissolving PNPX (manufactured by Sigma-Aldrich Co. LLC.) in water at a concentration of 3.4 mM was used as the substrate solution (hereafter also referred to as the "3.4 mM aqueous solution of PNPX"). The PNPX substrate solutions used in the experiments described below all used the 3.4 mM aqueous solution of PNPX prepared by the above method.

Specifically, a mixture solution containing 100 μL of the 3.4 mM aqueous solution of PNPX, 50 μL of a 200 mM acetate buffer (pH 4.0), 20 μL of the purified enzyme solution (10 ng/μL), and 30 μL of purified water was reacted at 70° C. for 20 minutes. In all measurements, a mixed solution prepared by replacing the gene recombinant E. coli homogenous supernatant or the purified enzyme with purified water and then reacting the solution under the same conditions was used as a control. Further, the substrate solution and the mixture of the purified enzyme solution and purified water and the buffer were held separately at the reaction temperatures for 5 minutes before being mixed to initiate the reaction. In each case, following completion of the reaction, the reaction was stopped by adding a 0.2 M Na$_2$CO$_3$ solution to the mixed solution in a volume equal to that of the mixed solution, and the resulting mixture was then centrifuged to obtain a supernatant. The amount of p-nitrophenol in the supernatant was determined by measuring the absorbance at 420 nm using a spectrophotometer, calculating the amount of p-nitrophenol in the supernatant using a calibration curve prepared with p-nitrophenol, and then determining the amount of p-nitrophenol produced by the enzymatic hydrolysis on the basis of the difference from the control. The enzymatic activity for producing 1 μmol of p-nitrophenol per minute was defined as 1 U, and the value obtained by dividing this activity by the amount of protein was defined as the specific activity (U/mg). Each measurement was performed for three independent experiments, and a mean value and a standard error were determined.

The results confirmed that both AR19M-311-2 and AR19M-311-11 had β-xylosidase activity (PNPX hydrolysis activity). The specific activity (U/mg) of AR19M-311-2 at 70° C. was 28.1 U/mg, and the specific activity (U/mg) of AR19M-311-11 at 70° C. was 25.6 U/mg. In the experiments described below, AR19M-311-2 was used as a result of its higher specific activity.

<9> Substrate Specificity of AR19M-311-2

The hydrolysis activity of AR19M-311-2 against various cellulose substrates and hemicellulose substrates was investigated. In the measurements, a purified enzyme solution prepared by diluting the purified enzyme obtained in section <7> above with water to obtain a concentration of 10 ng/μL was used. For the substrates, PSA, Avicel powder, CMC (manufactured by Sigma-Aldrich Co. LLC.), xylan (derived from beechwood, manufactured by Sigma-Aldrich Co. LLC.), lichenan (manufactured by MP Biomedicals Inc.), laminarin (derived from *Laminaria digitata*, manufactured by Sigma-Aldrich Co. LLC.), PNPX (manufactured by Sigma-Aldrich Co. LLC.) and PNPG (manufactured by Sigma-Aldrich Co. LLC.) were used.

The PSA was prepared by first dissolving Avicel powder (microcrystalline cellulose powder, manufactured by Merck & Co., Inc.) in a phosphoric acid solution, subsequently adding purified water to effect precipitation, and then performing washing until a pH of 5 or higher was reached. All the PSA used in the following experiments was prepared by this method.

Specifically, first, a reaction solution composed of a mixed solution containing 50 μL of 200 mM acetate buffer (pH 4.0), 20 μL of the purified enzyme solution (10 ng/μL) and 30 μL of purified water was preincubated at 70° C. for 5 minutes, 100 μL of one of the substrate solutions (a 1% by mass aqueous solution in the case of PSA, Avicel powder, CMC, xylan, lichenan or laminarin, or a 3.4 mM aqueous solution in the case of PNPX or PNPG) was then added, and the enzyme reaction was performed by incubating the resulting mixed solution at 70° C. for 20 minutes (or 2 hours in the case where Avicel powder was used as the substrate). In those cases where PSA, Avicel powder or xylan was used as the substrate, the mixed solution was agitated at 1400 rpm during the reaction using a Thermomixer (manufactured by the Eppendorf AG) so as to avoid the precipitation of insoluble substrate.

Following completion of the reaction, in the case of those reactions performed using PNPG or PNPX as the substrate, the same method as that described in section <8> above for investigating the PNPX hydrolysis activity of AR19M-311-2 was used to measure the absorbance at 420 nm of the supernatant of the reacted mixed solution, subsequently determine the amount of p-nitrophenol produced by the hydrolysis, and then calculate the specific activity (U/mg). In the case of the reactions performed using PSA, Avicel powder, CMC, xylan, lichenan or laminarin as the substrate, following completion of the reaction, 3,5-dinitrosalicylic acid reagent (DNS solution) was added to the reaction solution in a volume equal to that of the reaction solution, and the resulting mixture was heated at 100° C. for 5 minutes, cooled on ice for 5 minutes, and then centrifuged at 15,000 g for 5 minutes at 25° C. to obtain a supernatant. The absorbance at 540 nm was measured using a spectrophotometer, the amount of reduced sugar in the supernatant was calculated using a calibration curve prepared with glucose (or a calibration curve prepared with xylose in the case where xylan was used as the substrate), and the amount of reduced sugar produced by the enzymatic hydrolysis was calculated from the difference from the control. The enzymatic activity for producing 1 µmol of reduced sugar per minute was defined as 1 U, and the value obtained by dividing this activity by the mass of protein was defined as the specific activity (U/mg).

Figure 4:
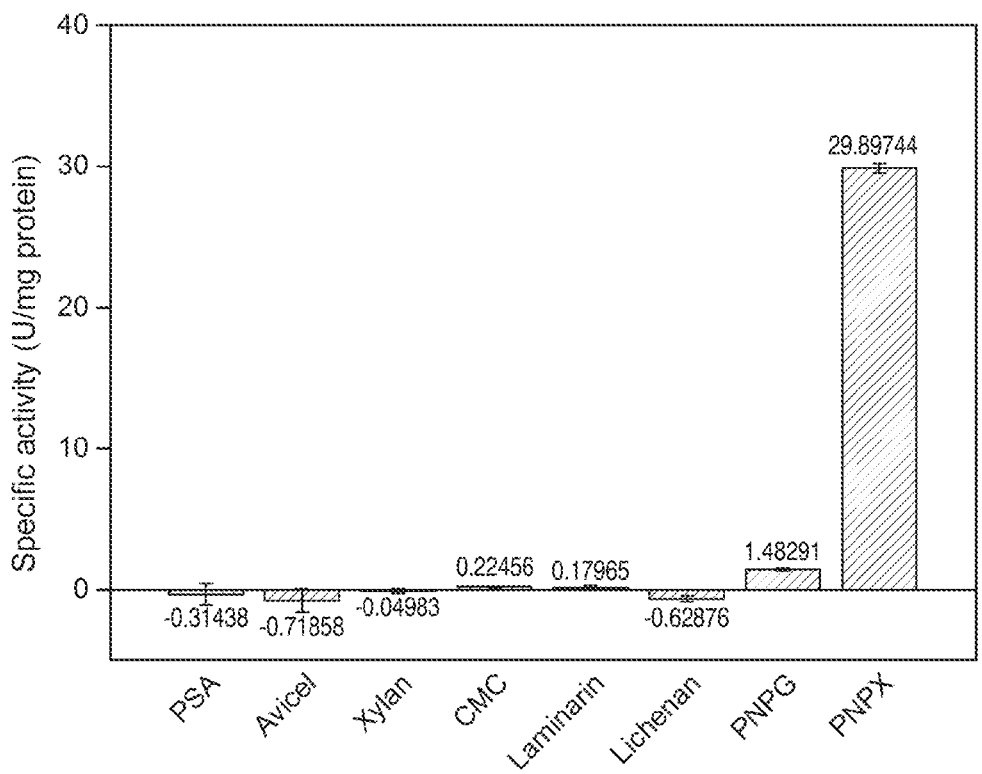
FIG. 4 is a diagram showing the results of measuring the hydrolysis activity of the AR19M-311-2 protein expressed in *E. coli* against various substrates in Example 1.

Each measurement was performed for three independent experiments, and a mean value and a standard error were determined. The measurement results are shown in FIG. 4. The results revealed that AR19M-311-2 exhibited a high level of hydrolysis activity against PNPX, and slight hydrolysis activity against PNPG. On the other hand, AR19M-311-2 exhibited almost no degradation activity against the other substrates.

<10> pH and Temperature Dependencies of β-Xylosidase Activity Against PNPX Substrate The temperature dependency and the pH dependency of the PNPX hydrolysis activity of AR19M-311-2 were investigated. In the measurements, a purified enzyme solution prepared by diluting the purified enzyme obtained in section <7> above with water to obtain a concentration of 10 ng/µL was used.

Measurement of the pH dependency of the PNPX hydrolysis activity of the purified AR19M-311-2 was conducted in the same manner as that described in section <8> above, with the exception of reacting a mixed solution containing 100 µL of the 3.4 mM aqueous solution of PNPX, 50 µL of McIlvaine's buffer (pH 3 to 8), 50 µL of acetate buffer (pH 3.5 to 6) or 50 µL of phosphate buffer (pH 6 to 8), 30 µL of purified water and 20 µL of the purified enzyme solution (10 ng/µL) at 70° C. for 20 minutes, and the amount of p-nitrophenol produced by the enzymatic hydrolysis was determined and the PNPX hydrolysis activity (U/mg) was calculated for each of the pH values.

Measurement of the temperature dependency of the PNPX hydrolysis activity of the purified AR19M-311-2 was conducted in the same manner as that described in section <8> above, with the exception of performing measurements at reaction temperatures of 30, 40, 50, 60, 65, 70, 75, 80, 85, 90, 95 and 100° C., and for each temperature, the amount of p-nitrophenol produced by the enzymatic hydrolysis was determined and the PNPX hydrolysis activity (U/mg) was calculated.

Figure 5:
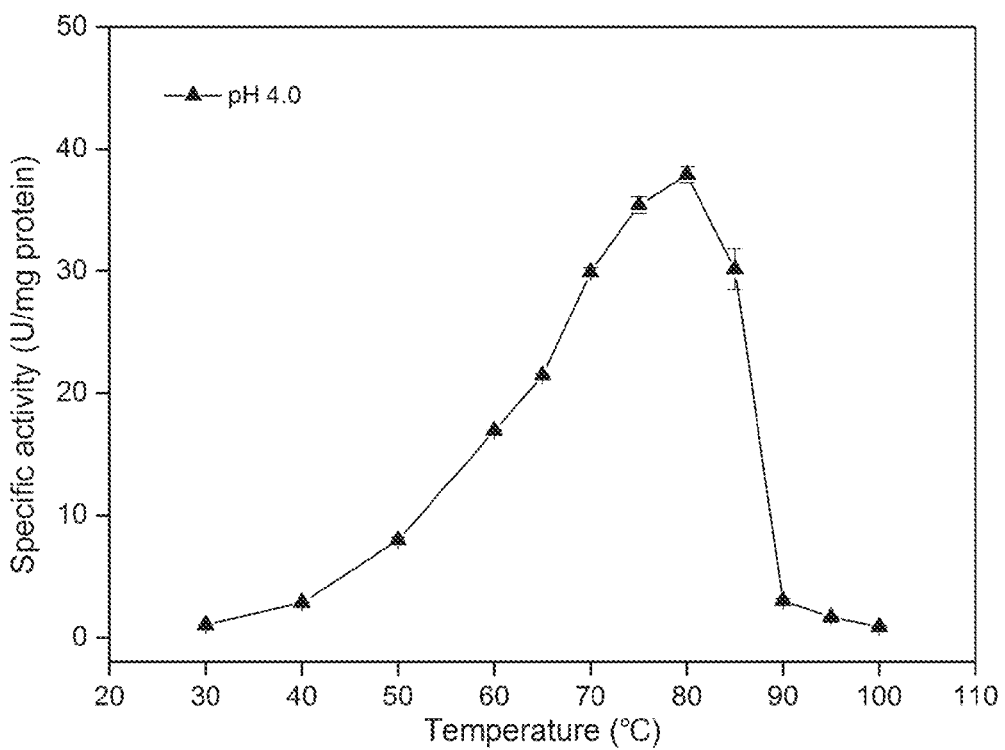
FIG. 5 is a diagram showing the results of measuring the PNPX hydrolysis activity (pH 4.0) of the AR19M-311-2 protein expressed in *E. coli* at various temperatures in Example 1.
Figure 6:
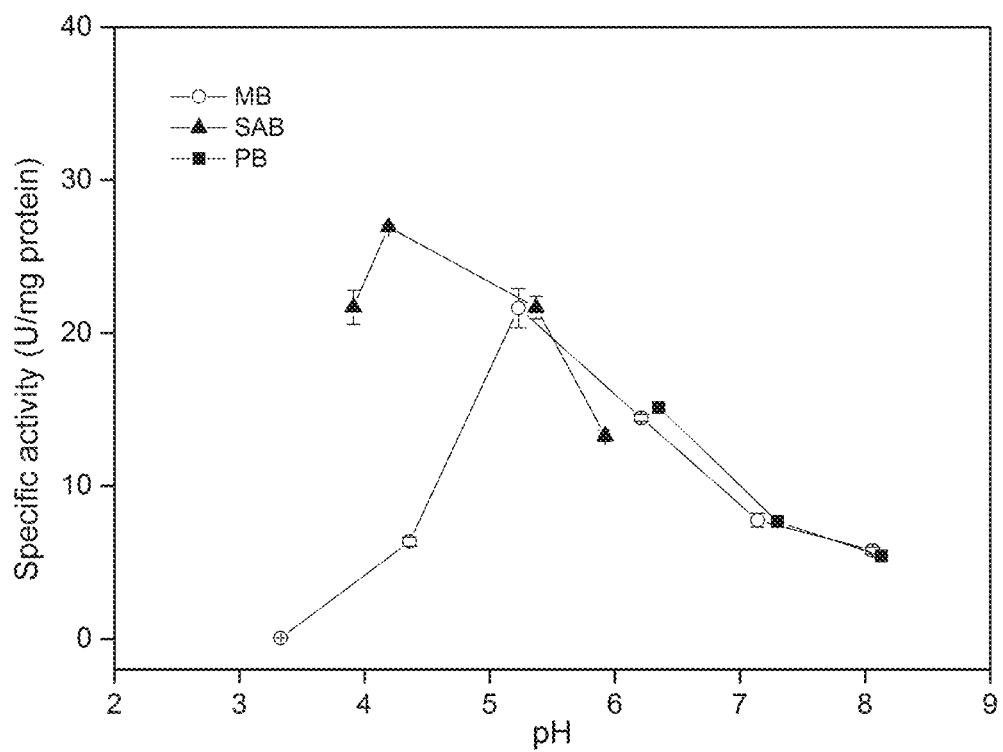
FIG. 6 is a diagram showing the results of measuring the PNPX hydrolysis activity (70° C.) of the AR19M-311-2 protein expressed in *E. coli* at various pH values in Example 1.

Each measurement was performed for three independent experiments, and a mean value and a standard error were determined. The measurement results are shown in FIG. 5 and FIG. 6. FIG. 5 is a graph showing the measurement results for the PNPX hydrolysis activity (pH 4.0) of the purified enzyme AR19M-311-2 at various temperatures, wherein the horizontal axis represents the temperature, and FIG. 6 is a graph showing the measurement results for the PNPX hydrolysis activity (70° C.) of the purified enzyme AR19M-311-2 at various pH values, wherein the horizontal axis represents the pH. In FIG. 6, "MB" indicates the results using McIlvaine's buffer (pH 3 to 8), "SAB" indicates the results using the acetate buffer (pH 3.5 to 6), and "PB" indicates the results using the phosphate buffer (pH 6 to 8). For the pH values, the actual measurement value obtained for the mixed solution containing the substrate, the buffer and the enzyme was plotted.

At a pH of 4.0, the purified enzyme AR19M-311-2 exhibited a high level of PNPX hydrolysis activity in a temperature range from 70 to 85° C. (FIG. 5). The optimum temperature ($T_{opt}$) showing the highest activity was 80° C. at a pH 4.0. When the enzymatic reaction temperature was set to 90° C. or higher at pH 4.0, the PNPX hydrolysis activity of the purified enzyme AR19M-311-2 decreased rapidly.

Moreover, the purified enzyme AR19M-311-2 exhibited PNPX hydrolysis activity in a pH range from 4.0 to 8.0 at a reaction temperature of 70° C. (FIG. 6). The optimum pH for the purified enzyme AR19M-311-2 at a reaction temperature of 70° C. was pH 4.19 (actual measurement value obtained for the mixed solution containing the substrate, the buffer and the enzyme).

<11> Thermal Stability Measurement of β-Xylosidase by Differential Scanning Fluorimetry Differential scanning fluorimetry (DSF) is one of the methods of measuring the thermal denaturation of proteins using a fluorescent dye and a real-time PCR machine, and can be applied to all manner of proteins. The fluorescent dyes used in DSF such as SYPRO Orange emit fluorescence under nonpolar conditions when bound to a hydrophobic region, while the emission is suppressed under the polar conditions produced upon dissolution in water. Usually, the protein structure unfolds at the thermal denaturation temperature, and the hydrophobic regions of the protein are exposed at the protein surface. When SYPRO Orange binds to such an exposed hydrophobic region, excitation light having a wavelength of 470 to 480 nm causes emission of a strong fluorescence having a peak near a wavelength of 595 nm By increasing the temperature of the protein solution at regular intervals in a stepwise manner and measuring the fluorescence intensity, the thermal degradation temperature (=change point of the fluorescence intensity) can be calculated.

Measurements were performed using a purified enzyme solution prepared by diluting the purified enzyme AR19M-311-2 obtained in section <7> above with water to obtain a concentration of 1 mg/mL.

Specifically, 2 µL of 100-fold diluted SYPRO Orange (manufactured by Life Technologies Inc.), 1 µL of the purified enzyme solution with a concentration of 1 mg/mL, 5 µL of 200 mM acetate buffer (pH 4.0) and 12 µL of purified water were added to each well of a 96-well PCR plate (Multiplate 96 Well PCR Plate MLL-9651, manufactured by Bio-Rad Laboratories, Inc.) so that the volume in each well was 20 µL. The PCR plate was sealed with Optical Flat 8-Cap Strips (manufactured by Bio-Rad Laboratories, Inc.), the temperature of each well was increased in steps of 0.2° C. from 30° C. up to 100° C. using a real-time PCR machine (CFX96 Touch Real-Time PCR System, manufactured by Bio-Rad Laboratories, Inc.), and following a pause of 10 seconds after each target temperature was achieved, the fluorescence intensity of each well was measured simultaneously. The SYPRO Orange was excited by a light emitting diode (LED) having a wavelength range of 450 to 490 nm, the emitted light from the SYPRO Orange was passed through a band pass filter having a range of 560 to 580 nm, a CCD camera was used to measure the fluorescence intensity, and the change in fluorescence intensity was plotted as a function of temperature. Data analysis was conducted using the analysis software CFX Manager (manufactured by Bio-Rad Laboratories, Inc.) supplied with the real-time PCR machine. Each measurement was performed by three independent experiments.

Figures 7A, 7B:
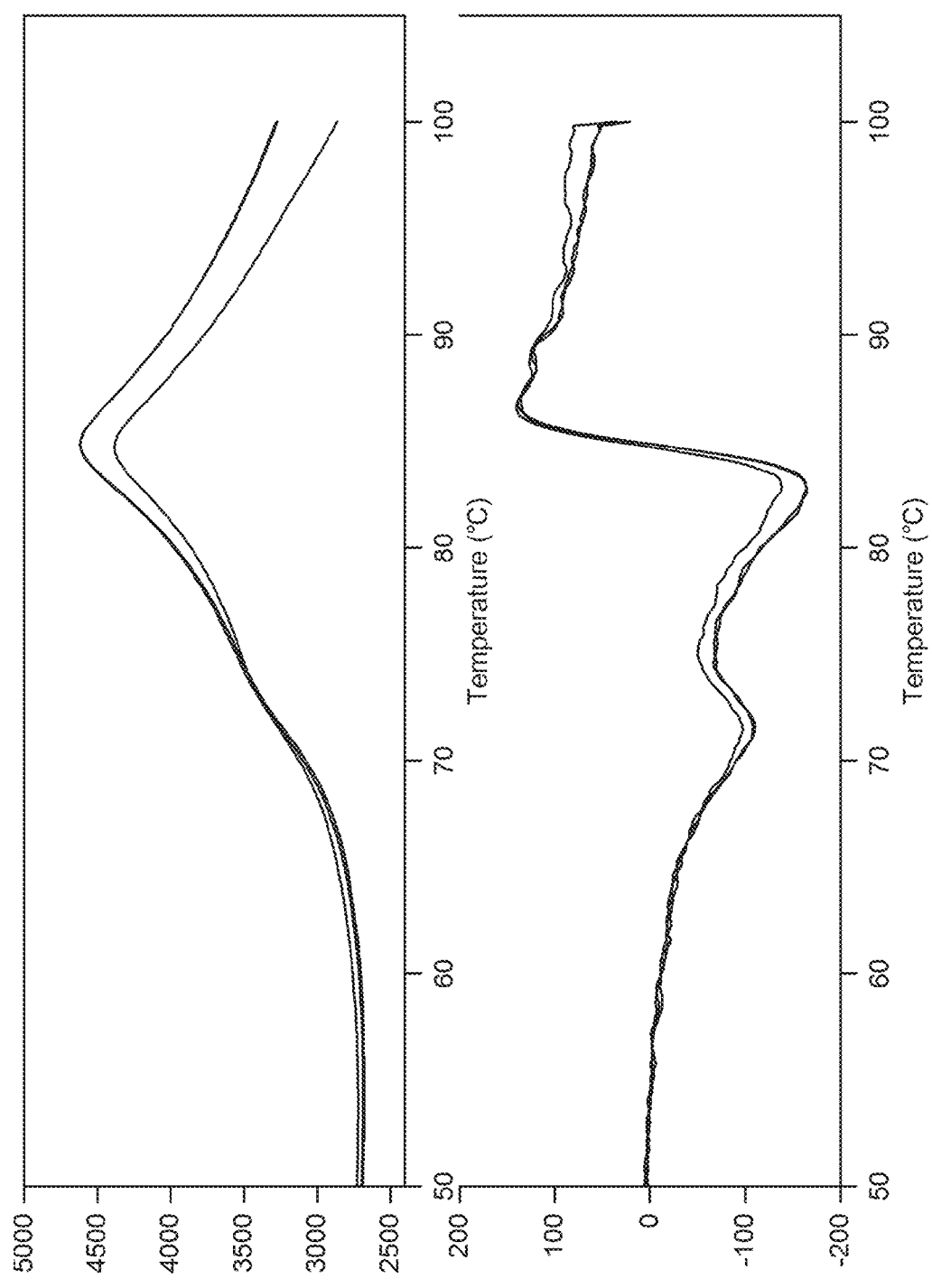
FIG. 7A is a diagram illustrating the actual measurement data of the change in the fluorescence intensity of SYPRO Orange caused in association with the thermal denaturation exhibited by the AR19M-311-2 protein expressed in *E. coli* in Example 1.
FIG. 7B is a diagram illustrating the first derivative "−d(Fluorescence)/dt" of the fluorescence intensity of SYPRO Orange caused in association with the thermal denaturation exhibited by the AR19M-311-2 protein expressed in *E. coli* in Example 1.

FIG. 7A and FIG. 7B shows the change in the fluorescence intensity of SYPRO Orange measured by the DSF method and caused in association with the thermal denaturation exhibited by the AR19M-311-2 enzyme protein. FIG. 7A shows the actual measurement data, and FIG. 7B shows the first derivative "−d(Fluorescence)/dt" of the fluorescence intensity change curve of FIG. 7A. The thermal denaturation temperature (melting temperature; Tm value) was defined as the local minimum value of the first derivative ("−d(Fluorescence)/dt" shown on the Y axis of FIG. 7B) of the fluorescence intensity curve that is a function of temperature. When the pH was 4.0, the first derivative of the fluorescence intensity for the AR19M-311-2 enzyme protein showed two local minimum points, at 71.5° C.±0.1 (n=3) and 82.7° C.±0.1 (n=3) respectively. Based on the fact that the optimum temperature determined from the PNPX hydrolysis activity was 80° C., it is thought that at the first local minimum point of 71.5° C., the enzyme protein undergoes some form of structural change, but does not lose its enzymatic activity. The second local minimum point is close to the optimum temperature $T_{opt}$=80° C. for the enzymatic activity, and it is thought that the temperature of this second local minimum point (82.7° C.) indicates the Tm of the enzyme.

[Sequence Listings]

```
SEQUENCE LISTING

<160> NUMBER OF SEQ ID NOS: 10

<210> SEQ ID NO 1
<211> LENGTH: 751
<212> TYPE: PRT
<213> ORGANISM: Unknown
<220> FEATURE:
<223> OTHER INFORMATION: Amino acid sequence encoded by an open reading
      frame AR19M-311; present in natural; obtained from microbial
      groups collected form high temperature hot spring soils; homology
      with an amino acid sequence of a beta-xylosidase (SEQ ID NO: 10)

<400> SEQUENCE: 1

Met Glu Glu Arg Trp Leu Gln Arg Arg Val Glu Glu Leu Leu Ser Lys
1               5                  10                  15

Met Thr Leu Glu Glu Lys Ile Ala Gln Leu Gly Ser Ile Pro Ser Gly
            20                  25                  30

Lys Leu Val Glu Asn Gly Lys Phe Ser Arg Glu Lys Ala Lys Glu Leu
        35                  40                  45

Leu Lys Asn Gly Ile Gly Gln Ile Thr Arg Val Ala Gly Tyr Ala Glu
    50                  55                  60

Arg Glu Pro Glu Ser Ile Glu Leu Ile Asn Glu Ile Gln Arg Phe
65                  70                  75                  80

Leu Lys Glu Glu Thr Arg Leu Gly Ile Pro Ala Ile Ile His Glu Glu
                85                  90                  95

Cys Leu Ser Gly Val Met Thr Lys Gly Ala Thr Thr Phe Pro Gln Ala
            100                 105                 110

Ile Gly Met Ala Ser Thr Phe Glu Pro Asp Asp Ile Gln Arg Met Thr
        115                 120                 125

Ser Ile Ile Arg Lys Glu Met Lys Ala Phe Gly Val His Gln Gly Leu
    130                 135                 140

Ser Pro Val Leu Asp Ile Pro Arg Asp Pro Arg Trp Gly Arg Thr Glu
145                 150                 155                 160

Glu Thr Phe Gly Glu Asp Pro Tyr Leu Val Ser Lys Met Ala Glu Ser
                165                 170                 175

Tyr Ile Lys Gly Leu Gln Gly Glu Asp Trp Arg Glu Gly Ile Ile Ala
            180                 185                 190

Thr Val Lys His Phe Thr Ala Tyr Gly Ile Ser Glu Gly Ala Arg Asn
        195                 200                 205

Leu Gly Pro Ala Arg Val Ser Glu Arg Glu Leu Arg Glu Val Phe Leu
    210                 215                 220

Phe Pro Phe Glu Val Ala Ile Arg Lys Ala Asn Ala Gly Ser Val Met
225                 230                 235                 240

Asn Ala Tyr His Glu Ile Asp Gly Val Pro Cys Ala Ser Ser Lys Phe
                245                 250                 255

Leu Leu Thr Lys Ile Leu Arg Glu Glu Trp Gly Phe Lys Gly Phe Val
            260                 265                 270
```

```
Val Ser Asp Tyr Ser Ala Ile Glu Met Leu His Thr Phe His Lys Val
            275                 280                 285
Ala Lys Asp Leu Lys Thr Ala Ala Ile Lys Ala Leu Glu Ala Gly Ile
290                 295                 300
Glu Ile Glu Leu Pro Glu Thr Lys Cys Tyr Gly Glu Pro Leu Leu Ser
305                 310                 315                 320
Ala Val Lys Glu Gly Lys Val Ser Val Ser Val Ile Asp Thr Ala Val
                325                 330                 335
Ala Arg Val Leu Arg Ala Lys Ile Leu Gly Leu Leu Asp Asp Ile
                340                 345                 350
Ile Tyr Val Asp Pro Ser Lys Ile Arg Ala Val Leu Asp Asn Pro Glu
            355                 360                 365
His Arg Ala Phe Ala Arg Glu Leu Ala Arg Lys Ser Ile Val Leu Leu
    370                 375                 380
Lys Asn Asp Gly Ile Leu Pro Ile Ser Lys Gly Val Lys Thr Ile Ala
385                 390                 395                 400
Val Ile Gly Pro Ser Ala Asp Ser Thr Lys Asn Leu His Gly Asp Tyr
                405                 410                 415
Ser Tyr Thr Ser His Ile Ala Gly Val Ala Asp Gly Val Arg Thr Val
                420                 425                 430
Thr Val Leu Glu Gly Ile Lys Asn Lys Val Ser Ser Gly Thr Thr Val
            435                 440                 445
Leu Tyr Ala Lys Gly Cys Glu Leu Ser Asp Glu Ser Arg Glu Gly Phe
    450                 455                 460
Lys Glu Ala Leu Asp Ile Ala Ser Arg Ser Asp Val Ile Ile Ala Val
465                 470                 475                 480
Met Gly Glu Asn Ser Gly Leu Phe Lys Arg Gly Ile Ser Gly Glu Gly
                485                 490                 495
Asn Asp Arg Ile Asp Leu Lys Leu Pro Gly Val Gln Glu Glu Leu Leu
            500                 505                 510
Lys Ala Leu Lys Glu Val Gly Lys Pro Ile Val Leu Val Leu Val Asn
    515                 520                 525
Gly Arg Pro Leu Ser Ile Lys Trp Glu Lys Glu Asn Ile Pro Ala Ile
530                 535                 540
Leu Glu Val Trp Tyr Pro Gly Glu Glu Gly Gly Asn Ala Ile Ala Asp
545                 550                 555                 560
Val Ile Phe Gly Asp Tyr Asn Pro Gly Gly Lys Leu Pro Ile Ser Phe
                565                 570                 575
Pro Lys Asp Val Gly Gln Ile Pro Val Tyr Tyr Asn Arg Lys Pro Ser
            580                 585                 590
Ala Phe Ser Glu Tyr Leu Thr Thr Asp Thr Lys Pro Leu Phe Pro Phe
    595                 600                 605
Gly His Gly Leu Ser Tyr Thr Thr Phe Glu Tyr Ser Glu Leu Lys Ile
    610                 615                 620
Ile Pro Glu Asn Val Met Pro Gly Gly Tyr Val Asp Ile Ser Phe Lys
625                 630                 635                 640
Val Arg Asn Thr Gly Asn Ile Asp Gly Asp Glu Val Val Gln Leu Tyr
                645                 650                 655
Ile His Asp Glu Trp Ala Ser Val Glu Arg Pro Ile Lys Glu Leu Lys
            660                 665                 670
Gly Phe Lys Arg Ile His Leu Lys Ala Arg Glu Glu Lys Lys Val Thr
    675                 680                 685
```

```
Phe Arg Leu Phe Thr Asp Gln Leu Ala Phe Tyr Asp Glu Val Met Arg
        690                 695                 700

Phe Val Val Glu Ala Gly Thr Phe Glu Val Met Val Gly Ser Ser Ser
705                 710                 715                 720

Glu Asp Ile Arg Leu Thr Gly Lys Phe Glu Val Leu Glu Thr Lys Val
                725                 730                 735

Ile Thr Lys Asp Arg Lys Phe Ala Ser Glu Val Ile Ile Glu Pro
            740                 745                 750

<210> SEQ ID NO 2
<211> LENGTH: 2256
<212> TYPE: DNA
<213> ORGANISM: Unknown
<220> FEATURE:
<223> OTHER INFORMATION: Nucleotide sequence of the open reading frame
      AR19M-311; present in natural; obtained from microbial groups
      collected form high temperature hot spring soils; has a homology
      with an amino acid sequence of a beta-xylosidase (SEQ ID NO: 10)

<400> SEQUENCE: 2
atggaagaaa gatggttaca agaagagtt gaagagttat tatcgaagat gactcttgaa      60
gaaaaaatag cccaacttgg ttcaatacca tcgggtaaac tagtagaaaa tggaaaattt    120
tctagagaaa aagccaaaga acttttgaaa atggtatag gacaaataac tagagtagca    180
ggatacgccg agagagagcc agaagaatcg atagaactta taaatgagat tcagagattt    240
ctaaaagagg agactagact aggtataccg gcaataattc acgaagagtg tctttcgggt    300
gtcatgacca aaggagcaac aacatttcca caggctatag ggatggctag cacatttgag    360
ccagacgata ttcaaagaat gacttccatt ataagaaaag agatgaaggc atttggtgtt    420
catcaagggc tctctcctgt ccttgatatt cctagggacc ctagatgggg aaggacagaa    480
gaaacatttg gagaagaccc atatcttgta tcaaagatgg cagaaagtta tataaaaggg    540
cttcagggag aagattggag agaaggaatt attgctacag ttaaacatt tacagcttac    600 ggtatttctg agggagcaag aaatttgggt cctgccagag tatctgaaag ggaattaaga    660
gaggtattcc tctttccatt tgaagtcgca ataagaaaag ccaatgctgg ttctgtaatg    720
aatgcctatc atgagataga tggggtccca tgtgcgtctt ccaagttttt actgacaaaa    780
atccttagag aagaatgggg attcaaagga tttgtagtct cagactattc agctatagag    840
atgttacata cattccacaa agtagctaaa gacctaaaga ctgcagctat aaaagcccta    900
gaggcaggaa ttgaaataga attaccagag acaaaatgtt atggtgaacc acttttatca    960
gcagtcaaag aaggaaaggt atctgtctct gttatagata ccgctgtagc tagagtctta   1020
agggcaagaa tactcctagg actattagat gatattatct acgtagatcc aagtaagata   1080
agagctgtct tagataaccc agagcacagg gcatttgcca gagaactagc tagaaaatct   1140
attgttttat taagaatga tggaatacta cccataagta aaggggtaaa aaccattgca   1200
gttataggtc cgagtgcaga tagtacaaaa atctacatg gagactatag ttataccca   1260 catatagcag gagtagcgga cggtgtaagg acagtaacag tgttagaggg tatcaaaaat   1320
aaagtgtcct caggaaccac tgtcctctat gctaagggct gtgaacttag tgatgaatct   1380
agagaaggat ttaaagaggc attagatata gctagtagat cagatgtcat tatagcggtg   1440
atgggagaaa atagcggact attaagaga ggaatctcag gagaaggtaa tgacaggata   1500
gatctaaaac ttccaggggt tcaagaggaa cttctaaagg ctttaaagga agtgggtaaa   1560
ccaattgtgc tagttctagt taatggaagg cccctctcta taaagtggga gaagaaaat   1620
```

```
atcccagcta ttctagaagt atggtatcca ggggaagaag gaggaaacgc aatagcagat   1680
gtaatatttg gagattataa cccaggaggg aagttaccaa tctcattccc aaaggatgtt   1740
ggacaaatac cagtctacta atatagaaag ccatctgcct ttagtgaata cttaacaaca   1800
gatactaaac ccttgtttcc atttggacat ggcttgagtt atacaacctt tgagtattca   1860
gaactaaaaa taatcccaga aaatgtcatg cccgggggat atgtagacat aagctttaaa   1920
gtaagaaata caggcaatat agacggagat gaagtagtgc aactttatat acatgatgaa   1980
tgggcaagtg tagaaagacc aataaaagaa ctaaagggt ttaagaggat tcacctaaaa   2040
gcaagagaag aaaagaaggt caccttcaga ttatttacag accagttagc attttatgat   2100
gaagtgatgc gatttgtggt agaagcaggg acatttgaag ttatggtagg gtcctcctca   2160
gaagatataa gattaacagg taagtttgag gtcttagaga ccaaggttat aacaaaggat   2220
agaaaatttg ctagcgaggt aattatagaa ccttaa                            2256
```

<210> SEQ ID NO 3
<211> LENGTH: 751
<212> TYPE: PRT
<213> ORGANISM: Unknown
<220> FEATURE:
<223> OTHER INFORMATION: Amino acid sequence of the AR19M-311-2 protein;
      present in natural; obtained from microbial groups collected form
      high temperature hot spring soils; has a homology with an amino
      acid sequence of a beta-xylosidase (SEQ ID NO: 10)

<400> SEQUENCE: 3

```
Met Glu Glu Arg Trp Leu Gln Arg Arg Val Glu Glu Leu Leu Ser Lys
1               5                   10                  15

Met Thr Leu Glu Glu Lys Ile Ala Gln Leu Gly Ser Ile Pro Ser Gly
            20                  25                  30

Lys Leu Val Glu Asn Gly Lys Phe Ser Arg Glu Lys Ala Lys Glu Leu
        35                  40                  45

Leu Lys Asn Gly Ile Gly Gln Ile Thr Arg Val Ala Gly Tyr Ala Glu
    50                  55                  60

Arg Glu Pro Glu Glu Ser Ile Glu Leu Ile Asn Glu Ile Gln Arg Phe
65                  70                  75                  80

Leu Lys Glu Glu Thr Arg Leu Gly Ile Pro Ala Ile Ile His Glu Glu
                85                  90                  95

Cys Leu Ser Gly Val Met Thr Lys Gly Ala Thr Thr Phe Pro Gln Ala
            100                 105                 110

Ile Gly Met Ala Ser Thr Phe Glu Pro Asp Asp Ile Gln Arg Met Thr
        115                 120                 125

Ser Ile Ile Arg Lys Glu Met Lys Ala Phe Gly Val His Gln Gly Leu
    130                 135                 140

Ser Pro Val Leu Asp Ile Pro Arg Asp Pro Arg Trp Gly Arg Thr Glu
145                 150                 155                 160

Glu Thr Phe Gly Glu Asp Pro Tyr Leu Val Ser Lys Met Ala Glu Ser
                165                 170                 175

Tyr Ile Lys Gly Leu Gln Gly Glu Asp Trp Lys Gly Ile Ile Ala
            180                 185                 190

Thr Ala Lys His Phe Thr Ala Tyr Gly Ile Ser Glu Gly Gly Arg Asn
        195                 200                 205

Leu Gly Pro Ala Arg Val Ser Glu Arg Glu Leu Arg Glu Val Phe Leu
    210                 215                 220

Phe Pro Phe Glu Val Ala Ile Arg Lys Ala Asn Ala Gly Ser Val Met
225                 230                 235                 240
```

-continued

Asn Ala Tyr His Glu Ile Asp Gly Val Pro Cys Ala Ser Ser Lys Phe
            245                 250                 255

Leu Leu Thr Lys Ile Leu Arg Glu Glu Trp Gly Phe Lys Gly Phe Val
        260                 265                 270

Val Ser Asp Tyr Ser Ala Ile Glu Met Leu His Thr Phe His Lys Val
    275                 280                 285

Ala Lys Asp Leu Lys Thr Ala Ile Lys Ala Leu Glu Ala Gly Ile
290                 295                 300

Glu Ile Glu Leu Pro Glu Ile Lys Cys Tyr Gly Glu Pro Leu Leu Ser
305                 310                 315                 320

Ala Val Lys Glu Gly Lys Val Ser Val Ser Val Ile Asp Thr Ala Val
                325                 330                 335

Ala Arg Val Leu Arg Ala Lys Ile Leu Leu Gly Leu Leu Asp Asp Ile
            340                 345                 350

Ile Tyr Ala Asp Pro Ser Lys Ile Arg Ala Val Leu Asp Asn Pro Glu
        355                 360                 365

His Arg Ala Phe Ala Arg Glu Leu Ala Arg Lys Ser Ile Val Leu Leu
    370                 375                 380

Lys Asn Asp Gly Ile Leu Pro Ile Ser Lys Gly Val Lys Thr Ile Ala
385                 390                 395                 400

Val Ile Gly Pro Ser Ala Asp Ser Thr Lys Asn Leu His Gly Asp Tyr
                405                 410                 415

Ser Tyr Thr Ser His Ile Ala Gly Val Ala Asp Gly Val Arg Thr Val
            420                 425                 430

Thr Val Leu Glu Gly Ile Lys Asn Lys Val Ser Ser Gly Thr Thr Val
        435                 440                 445

Leu Tyr Ala Lys Gly Cys Glu Leu Ser Asp Glu Ser Arg Glu Gly Phe
    450                 455                 460

Lys Glu Ala Leu Asp Ile Ala Ser Arg Ser Asp Val Ile Ile Ala Val
465                 470                 475                 480

Met Gly Glu Asn Ser Gly Leu Phe Lys Arg Gly Ile Ser Gly Glu Gly
                485                 490                 495

Asn Asp Arg Ile Asp Leu Lys Leu Pro Gly Val Gln Glu Glu Leu Leu
            500                 505                 510

Lys Ala Leu Lys Glu Val Gly Lys Pro Ile Val Leu Val Leu Val Asn
        515                 520                 525

Gly Arg Pro Leu Ser Ile Lys Trp Glu Lys Glu Asn Ile Pro Ala Ile
    530                 535                 540

Leu Glu Val Trp Tyr Pro Gly Glu Glu Gly Asn Ala Ile Ala Asp
545                 550                 555                 560

Val Ile Phe Gly Asp Tyr Asn Pro Gly Gly Lys Leu Pro Ile Ser Phe
                565                 570                 575

Pro Lys Asp Val Gly Gln Ile Pro Val Tyr Tyr Asn Arg Lys Pro Ser
            580                 585                 590

Ala Phe Ser Glu Tyr Leu Thr Thr Asp Thr Lys Pro Leu Phe Pro Phe
        595                 600                 605

Gly His Gly Leu Ser Tyr Thr Thr Phe Glu Tyr Ser Glu Leu Lys Ile
    610                 615                 620

Ile Pro Glu Asn Val Met Pro Gly Gly Tyr Ile Asp Ile Ser Phe Lys
625                 630                 635                 640

Val Arg Asn Thr Gly Asn Ile Asp Gly Asp Glu Val Val Gln Leu Tyr
                645                 650                 655

```
Ile His Asp Glu Trp Ala Ser Val Glu Arg Pro Ile Lys Glu Leu Lys
            660                 665                 670

Gly Phe Lys Arg Ile His Leu Lys Ala Arg Glu Glu Lys Lys Val Thr
        675                 680                 685

Phe Arg Leu Phe Thr Asp Gln Leu Ala Phe Tyr Asp Glu Val Met Arg
    690                 695                 700

Phe Val Glu Ala Gly Thr Phe Glu Val Met Val Gly Ser Ser Ser
705                 710                 715                 720

Glu Asp Ile Arg Leu Thr Gly Lys Phe Glu Val Leu Glu Thr Lys Val
                725                 730                 735

Ile Thr Lys Asp Arg Lys Phe Ala Ser Glu Val Ile Ile Glu Pro
            740                 745                 750
```

<210> SEQ ID NO 4
<211> LENGTH: 2256
<212> TYPE: DNA
<213> ORGANISM: Unknown
<220> FEATURE:
<223> OTHER INFORMATION: Nucleotide sequence encoding the amino acid
      sequence of AR19M-311-2; present in natural; obtained from
      microbial groups collected form high temperature hot spring soils;
      has a homology with an amino acid sequence of a beta-xylosidase
      (SEQ ID NO: 10)

<400> SEQUENCE: 4

```
atggaagaaa gatggttaca agaagagtt gaagagttat tatcgaagat gactcttgaa      60
gaaaaaatag cccaacttgg ttcaatacca tcgggtaaac tagtagaaaa tggaaaattt     120
tctagagaaa aagccaaaga acttttgaaa atggtatag acaaataac tagagtagca       180 ggatacgccg agagagagcc agaagaatcg atagaactta taaatgagat tcagagattt     240
ctaaaagagg agactagact aggtataccg gcaataattc acgaagagtg tctttcgggt     300
gtcatgacca aaggagcaac aacatttcca caggctatag ggatggctag cacatttgag     360
ccagacgata ttcaaagaat gacttccatt ataagaaaag agatgaaggc atttggtgtt     420
catcaagggc tctctcctgt ccttgatatt cctagggacc ctagatgggg aaggacagaa     480
gaaacatttg agaagacccc atatcttgta tcaaagatgg cagaaagtta tataaagggg     540
cttcagggag aagattggaa ggagggtata attgctaccg ctaaacattt tacagcttac     600
ggtatatcgg aaggtggtag aaatctgggc cctgccagag tatctgaaag ggaattaaga     660
gaggtattcc tctttccatt tgaagtcgca ataagaaaag ccaatgctgg ttctgtaatg     720
aatgcctatc atgagataga tggggtccca tgtgcgtctt ccaagttttt actgacaaaa     780
atccttagag aagaatgggg attcaaagga tttgtagtct cagactattc agctatagag     840
atgttacata cattccacaa agtagctaaa gacctaaaga ctgcagctat aaaagcccta     900
gaggcaggaa ttgaaataga attaccagag ataaaatgtt atggtgaacc actttatca      960 gcagtcaaag aaggaaaggt atctgtctct gttatagata ccgctgtagc tagagtctta    1020
agggcaaaga tactcctagg actattagat gatattatct acgcagatcc aagtaagata    1080
agagctgtct tagataaccc agagcacagg gcatttgcca gagaactagc tagaaaatct    1140
attgttttat taagaatgat ggaatactaa cccataagta aaggggtaaa aaccattgca    1200
gttataggtc cgagtgcaga tagcacaaaa atctacatg gagactatag ttatacctca     1260
catatagcag gagtagcgga cggtgtaagg acagtaacag tgttagaggg tatcaaaaat    1320
aaagtgtcct caggaaccac tgtcctctat gctaagggct gtgaacttag tgatgaatct    1380
agagaaggat ttaaagaggc attagataata gctagtagat cagatgtcat tatagcggtg    1440
```

```
atgggagaaa atagcggact atttaagaga ggaatctcag gagaaggtaa tgacaggata    1500
gatctaaaac ttccaggggt tcaagaggaa cttctaaagg cttttaaagga agtgggtaaa    1560 ccaattgtgc tagttctagt taatggaagg ccctctcta taaagtggga gaaagaaaat    1620
atcccagcta ttctagaagt atggtatcca ggggaagaag gaggaaacgc aatagcagat    1680
gtaatatttg gagattataa cccaggaggg aagttaccaa tctcattccc aaaggatgtt    1740
ggacaaatac cagtctacta taatagaaag ccatctgcct ttagtgaata cttaacaaca    1800
gatactaaac ccttgtttcc atttggacat ggcttgagtt atacaacctt tgagtattca    1860
gaactaaaaa taatcccaga aaatgtcatg cccgggggat atatagacat aagctttaaa    1920
gtaagaaata caggcaatat agacggagat gaagtagtgc aactttatat acatgatgaa    1980
tgggcaagtg tagaaagacc aataaaagaa ctaaaagggt ttaagaggat tcacctaaaa    2040
gcaagagaag aaaagaaggt caccttcaga ttatttacag accagttagc atttttatgat    2100 gaagtgatgc gatttgtggt agaagcaggg acatttgaag ttatggtagg gtcctcctca    2160
gaagatataa gattaacagg taagtttgag gtcttagaga ccaaggttat aacaaggat    2220 agaaaatttg ctagcgaggt aattatagaa ccttaa                             2256
```

<210> SEQ ID NO 5
<211> LENGTH: 751
<212> TYPE: PRT
<213> ORGANISM: Unknown
<220> FEATURE:
<223> OTHER INFORMATION: Amino acid sequence of AR19M-311-11; present in natural; obtained from microbial groups collected form high temperature hot spring soils; has a homology with an amino acid sequence of a beta-xylosidase (SEQ ID NO: 10)

<400> SEQUENCE: 5

```
Met Glu Glu Arg Trp Leu Gln Arg Arg Val Glu Glu Leu Leu Ser Lys
1               5                   10                  15

Met Thr Leu Glu Glu Lys Ile Ala Gln Leu Gly Ser Ile Pro Ser Gly
            20                  25                  30

Lys Leu Val Glu Asn Gly Lys Phe Ser Arg Glu Lys Ala Lys Glu Leu
        35                  40                  45

Leu Lys Asn Gly Ile Gly Gln Ile Thr Arg Val Ala Gly Tyr Ala Glu
    50                  55                  60

Arg Glu Pro Glu Ser Ile Glu Leu Ile Asn Glu Ile Gln Arg Phe
65                  70                  75                  80

Leu Lys Glu Glu Thr Arg Leu Gly Ile Pro Ala Ile Ile His Glu Glu
                85                  90                  95

Cys Leu Ser Gly Val Met Thr Lys Gly Ala Thr Thr Phe Pro Gln Ala
            100                 105                 110

Ile Gly Met Ala Ser Thr Phe Glu Pro Asp Asp Ile Gln Arg Met Thr
        115                 120                 125

Ser Ile Ile Arg Lys Glu Met Lys Ala Phe Gly Val His Gln Gly Leu
    130                 135                 140

Ser Pro Val Leu Asp Ile Pro Arg Asp Pro Arg Trp Gly Arg Thr Glu
145                 150                 155                 160

Glu Thr Phe Gly Glu Asp Pro Tyr Leu Val Ser Lys Met Ala Glu Ser
                165                 170                 175

Tyr Ile Lys Gly Leu Gln Gly Glu Asp Trp Lys Glu Gly Ile Ile Ala
            180                 185                 190

Thr Ala Lys His Phe Thr Ala Tyr Gly Ile Ser Glu Gly Gly Arg Asn
        195                 200                 205
```

```
Leu Gly Pro Ala Arg Val Ser Glu Arg Glu Leu Arg Glu Val Phe Leu
    210                 215                 220

Phe Pro Phe Glu Val Ala Ile Arg Lys Ala Asn Ala Gly Ser Val Met
225                 230                 235                 240

Asn Ala Tyr His Glu Ile Asp Gly Val Pro Cys Ala Ser Ser Lys Phe
                245                 250                 255

Leu Leu Thr Lys Ile Leu Arg Glu Glu Trp Gly Phe Lys Gly Phe Val
            260                 265                 270

Val Ser Asp Tyr Ser Ala Ile Glu Met Leu His Thr Phe His Lys Val
        275                 280                 285

Ala Lys Asp Leu Lys Thr Ala Ala Ile Lys Ala Leu Glu Ala Gly Ile
290                 295                 300

Glu Ile Glu Leu Pro Glu Ile Lys Cys Tyr Gly Glu Pro Leu Leu Ser
305                 310                 315                 320

Ala Val Lys Glu Gly Lys Val Ser Val Ser Val Ile Asp Thr Ala Val
                325                 330                 335

Ala Arg Val Leu Arg Ala Lys Ile Leu Leu Gly Leu Leu Asp Asp Ile
            340                 345                 350

Ile Tyr Val Asp Pro Ser Lys Ile Arg Ala Val Leu Asp Asn Pro Glu
        355                 360                 365

His Arg Ala Phe Ala Arg Glu Leu Ala Arg Lys Ser Ile Val Leu Leu
370                 375                 380

Lys Asn Asp Gly Ile Leu Pro Ile Ser Lys Gly Val Lys Thr Ile Ala
385                 390                 395                 400

Val Ile Gly Pro Ser Ala Asp Ser Thr Lys Asn Leu His Gly Asp Tyr
                405                 410                 415

Ser Tyr Thr Ser His Ile Ala Gly Val Ala Asp Gly Val Arg Thr Val
            420                 425                 430

Thr Val Leu Glu Gly Ile Lys Asn Lys Val Ser Ser Gly Thr Thr Val
        435                 440                 445

Leu Tyr Ala Lys Gly Cys Glu Leu Ser Asp Glu Ser Arg Glu Gly Phe
450                 455                 460

Lys Glu Ala Leu Asp Ile Ala Ser Arg Ser Asp Val Ile Ile Ala Val
465                 470                 475                 480

Met Gly Glu Asn Ser Gly Leu Phe Lys Arg Gly Ile Ser Gly Glu Gly
                485                 490                 495

Asn Asp Arg Ile Asp Leu Lys Leu Pro Gly Val Gln Glu Glu Leu Leu
            500                 505                 510

Lys Ala Leu Lys Glu Val Gly Lys Pro Ile Val Leu Val Leu Val Asn
        515                 520                 525

Gly Arg Pro Leu Ser Ile Lys Trp Glu Lys Glu Asn Ile Pro Ala Ile
530                 535                 540

Leu Glu Val Trp Tyr Pro Gly Glu Glu Gly Asn Ala Ile Ala Asp
545                 550                 555                 560

Val Ile Phe Gly Asp Tyr Asn Pro Gly Gly Lys Leu Pro Ile Ser Phe
                565                 570                 575

Pro Lys Asp Val Gly Gln Ile Pro Val Tyr Tyr Asn Arg Lys Pro Ser
            580                 585                 590

Ala Phe Ser Glu Tyr Leu Thr Thr Asp Thr Lys Pro Leu Phe Pro Phe
        595                 600                 605

Gly His Gly Leu Ser Tyr Thr Thr Phe Glu Tyr Ser Glu Leu Lys Ile
610                 615                 620
```

| | | | | | | | | | | | | |
|---|---|---|---|---|---|---|---|---|---|---|---|---|
|Ile|Pro|Glu|Asn|Val|Met|Pro|Gly|Gly|Tyr|Val|Asp|Ile|Ser|Phe|Lys|
|625| | | | |630| | | | |635| | | | |640|

| | | | | | | | | | | | | |
|---|---|---|---|---|---|---|---|---|---|---|---|---|
|Val|Arg|Asn|Thr|Gly|Asn|Ile|Asp|Gly|Asp|Glu|Val|Val|Gln|Leu|Tyr|
| | | | |645| | | | |650| | | | |655| |

| | | | | | | | | | | | | |
|---|---|---|---|---|---|---|---|---|---|---|---|---|
|Ile|His|Asp|Glu|Trp|Ala|Ser|Val|Glu|Arg|Pro|Ile|Lys|Glu|Leu|Lys|
| | | |660| | | | |665| | | | |670| | |

| | | | | | | | | | | | | |
|---|---|---|---|---|---|---|---|---|---|---|---|---|
|Gly|Phe|Lys|Arg|Ile|His|Leu|Lys|Ala|Arg|Glu|Glu|Lys|Lys|Val|Thr|
| | |675| | | | |680| | | | |685| | | |

| | | | | | | | | | | | | |
|---|---|---|---|---|---|---|---|---|---|---|---|---|
|Phe|Arg|Leu|Phe|Thr|Asp|Gln|Leu|Ala|Phe|Tyr|Asp|Glu|Val|Met|Arg|
| |690| | | | |695| | | | |700| | | | |

| | | | | | | | | | | | | |
|---|---|---|---|---|---|---|---|---|---|---|---|---|
|Phe|Val|Val|Glu|Ala|Gly|Thr|Phe|Glu|Val|Met|Val|Gly|Ser|Ser|Ser|
|705| | | | |710| | | | |715| | | | |720|

| | | | | | | | | | | | | |
|---|---|---|---|---|---|---|---|---|---|---|---|---|
|Glu|Asp|Ile|Arg|Leu|Thr|Gly|Lys|Phe|Glu|Val|Leu|Glu|Thr|Lys|Val|
| | | | |725| | | | |730| | | | |735| |

| | | | | | | | | | | |
|---|---|---|---|---|---|---|---|---|---|---|
|Ile|Thr|Lys|Asp|Arg|Lys|Phe|Ala|Ser|Glu|Val|Ile|Ile|Glu|Pro|
| | | |740| | | | |745| | | | |750| |

<210> SEQ ID NO 6
<211> LENGTH: 2256
<212> TYPE: DNA
<213> ORGANISM: Unknown
<220> FEATURE:
<223> OTHER INFORMATION: Nucleotide sequence encoding the amino acid
      sequence of AR19M-311-11; present in natural; obtained from
      microbial groups collected form high temperature hot spring soils;
      has a homology with an amino acid sequence of a beta-xylosidase
      (SEQ ID NO: 10)

<400> SEQUENCE: 6

```
atggaagaaa gatggttaca aagaagagtt gaagagttat tatcgaagat gactcttgaa      60
gaaaaaatag cccaacttgg ttcaatacca tcgggtaaac tagtagaaaa tggaaaattt     120
tctagagaaa agccaaagaa acttttgaaa atggtatag  gacaaataac tagagtagca     180
ggatacgccg agagagagcc agaagaatcg atagaactta taatgagat tcagagattt      240
ctaaaagagg agactagact aggtataccg gcaataattc acgaagagtg tctttcgggt     300
gtcatgacca aaggagcaac aacatttcca caggctatag  ggatggctag cacatttgag    360
ccagacgata ttcaaagaat gacttccatt ataagaaaag agatgaaggc atttggtgtt     420
catcaagggc tctctcccgt ccttgatatt cctaggagacc ctagatgggg aaggacagaa    480
gaaacatttg agaagacccc atatcttgta tcaaagatgg cagaaagtta tataaaaggg    540
cttcagggag aagattggaa ggaaggtata attgctaccg ctaaacattt tacagcttac    600
ggtatatcgg aaggtggtag aaatctgggc cctgccagag tatctgaaag ggaattaaga    660
gaggtattcc tatttccatt tgaagtcgca ataagaaaag ccaatgctgg ttctgtaatg    720
aatgcctatc atgagataga tggggtccca tgtgcgtctt ccaagttttt actgacaaaa    780
atccttagag aagaatgggg attcaaagga tttgtagtct cagactattc agctatagag    840
atgttacata cattccacaa agtagctaaa gacctaaaga ctgcagctat aaaagcccta    900
gaggcaggaa ttgaaataga attaccagag ataaaatgtt atggtgaacc acttttatca    960
gcagtcaaag aaggaaaggt atctgtctct gttatagata ccgctgtagc tagagtctta   1020
agggcaaaga tactcctagg actattagat gatattatct acgtagatcc aagtaagata   1080
agagccgtct tagataaccc agagcatagg gcatttgcca gagaactagc tagaaaatct   1140
attgttttat taagaatgga tggaaatacta cccataagta aagggtaaa aaccattgca   1200
gttataggtc cgagtgcaga tagcacaaaa aatctacatg gagactatag ttatacctca   1260
```

```
catatagcag gagtagcgga cggtgtaagg acagtaacag tgttagaggg tatcaaaaat    1320
aaagtgtcct caggaaccac tgtcctctat gctaagggct gtgaacttag tgatgaatct    1380
agagaaggat ttaaagaggc attagatata gctagtagat cagatgtcat tatagcggtg    1440
atgggagaaa atagcggact atttaagaga ggaatctcag gagaaggtaa tgacaggata    1500
gatctaaaac ttccaggggt tcaagaggaa cttctaaagg ctttaaagga agtgggtaaa    1560
ccaattgtgc tagttctagt taatggaagg cccctctcta taaagtggga gaagaaaat     1620 atcccagcta ttctagaagt atggtatcca ggggaagaag gaggaaacgc aatagcagat    1680
gtaatatttg gagattataa cccaggaggg aagttaccaa tctcattccc aaaggatgtt    1740
ggacaaatac cagtctacta taatagaaag ccatctgcct ttagtgaata cttaacaaca    1800
gatactaaac ccttgtttcc atttggacat ggcttgagtt atacaacctt tgagtattca    1860
gaactaaaaa taatcccaga aaatgtcatg cccgggggat atgtagacat aagctttaaa    1920
gtaagaaata caggcaatat agacggagat gaagtagtgc aactttatat acatgatgaa    1980
tgggcaagtg tagaaagacc aataaaagaa ctaaaagggt ttaagaggat tcacctaaaa    2040
gcaagagaag aaaagaaggt caccttcaga ttatttacag accagttagc attttatgat    2100
gaagtgatgc gatttgtggt agaagcaggg acatttgaag ttatggtagg gtcctcctca    2160
gaagatataa gattaacagg taagtttgag gtcttagaga ccaaggttat aacaaaggat    2220
agaaaatttg ctagcgaggt aattatagaa ccttaa                              2256

<210> SEQ ID NO 7
<211> LENGTH: 23
<212> TYPE: DNA
<213> ORGANISM: Artificial Sequence
<220> FEATURE:
<223> OTHER INFORMATION: Artificially synthesized; homologous
      (identical) with the partial sequence composed of the nucleotides
      from positions 1 to 23 of the nucleotide sequence of SEQ ID NO: 2,
      4 or 6; a partial sequence for design of SEQ ID NO: 9 primer

<400> SEQUENCE: 7
atggaagaaa gatggttaca aag                                              23

<210> SEQ ID NO 8
<211> LENGTH: 26
<212> TYPE: DNA
<213> ORGANISM: Artificial Sequence
<220> FEATURE:
<223> OTHER INFORMATION: Reverse primer having a nucleotide sequence
      which is complementary with the partial sequence composed of the
      nucleotides from positions 2,231 to 2,256 of the nucleotide
      sequence of SEQ ID NO: 2, 4 or 6; artificially synthesized

<400> SEQUENCE: 8
ttaaggttct ataattacct cgctag                                           26

<210> SEQ ID NO 9
<211> LENGTH: 27
<212> TYPE: DNA
<213> ORGANISM: Artificial Sequence
<220> FEATURE:
<223> OTHER INFORMATION: Forward primer in which 4 nucleotides (CACC)
      were added to the 5'-end of the nucleotide sequence of SEQ ID NO:
      7; artificially synthesized

<400> SEQUENCE: 9
caccatggaa gaaagatggt tacaaag                                          27
```

<210> SEQ ID NO 10
<211> LENGTH: 762
<212> TYPE: PRT
<213> ORGANISM: Unknown
<220> FEATURE:
<223> OTHER INFORMATION: Amino acid sequence of a beta-xylosidase belonging to the GH3 family of Dictyoglomus thermophilum; present in natural

<400> SEQUENCE: 10

```
Met Glu Glu Lys Glu Leu Ser Lys Lys Val Lys Asp Leu Ile Ala Lys
1               5                   10                  15

Met Thr Leu Glu Glu Lys Ile Ala Gln Leu Gln Ala Val Tyr Gly Lys
            20                  25                  30

Asp Leu Val Asp Glu Asn Gly Asn Phe Ser Glu Lys Ala Glu Lys
        35                  40                  45

Leu Leu Lys Asn Gly Ile Gly Gln Ile Ser Arg Val Ala Gly Glu Arg
    50                  55                  60

Gly Val Ser Pro Glu Lys Ala Val Glu Leu Ala Asn Lys Ile Gln Lys
65                  70                  75                  80

Phe Leu Lys Glu Lys Thr Arg Leu Gly Ile Pro Ala Ile Ile His Glu
                85                  90                  95

Glu Cys Leu Ser Gly Phe Met Ala Gln Gly Ala Thr Val Phe Pro Gln
            100                 105                 110

Ala Ile Gly Met Ala Ser Thr Phe Glu Pro Glu Leu Ile Arg Arg Val
        115                 120                 125

Ser Asp Val Ile Arg Gln His Met Lys Ala Ala Asn Val His Gln Gly
    130                 135                 140

Leu Ser Pro Val Leu Asp Ile Pro Arg Asp Pro Arg Trp Gly Arg Thr
145                 150                 155                 160

Glu Glu Thr Phe Gly Glu Asp Pro Tyr Leu Val Ser Arg Met Ala Thr
                165                 170                 175

Glu Tyr Val Lys Gly Leu Gln Gly Glu Asp Trp Arg Glu Gly Ile Val
            180                 185                 190

Ala Thr Val Lys His Phe Thr Ala Tyr Gly Ile Ser Glu Gly Ala Arg
        195                 200                 205

Asn Leu Gly Pro Ala Lys Val Gly Glu Arg Glu Leu Arg Glu Val Phe
    210                 215                 220

Leu Phe Pro Phe Glu Val Ala Ile Lys Glu Gly Gln Ala Gly Ser Leu
225                 230                 235                 240

Met Asn Ala Tyr His Glu Ile Asp Gly Val Pro Cys Ala Ser Ser Lys
                245                 250                 255

Phe Leu Leu Thr Lys Ile Leu Arg Trp Glu Trp Gly Phe Lys Gly Tyr
            260                 265                 270

Val Val Ser Asp Tyr Ile Ala Val Arg Met Leu Glu Asn Phe His Lys
        275                 280                 285

Val Ala Arg Asp Ala Lys Glu Ala Val Leu Ala Leu Glu Ala Gly
    290                 295                 300

Ile Asp Ile Glu Leu Pro Ser Val Asp Cys Tyr Gly Glu Pro Leu Ile
305                 310                 315                 320

Gln Ala Val Lys Glu Gly Leu Ile Ser Glu Glu Val Ile Asn Ala Ser
                325                 330                 335

Val Glu Arg Val Leu Arg Ala Lys Phe Met Leu Gly Leu Phe Asp Asp
            340                 345                 350
```

```
Asn Leu Glu Lys Asp Pro Lys Lys Val Tyr Glu Val Phe Asp Lys Pro
            355                 360                 365

Glu Phe Arg Asp Leu Ser Arg Glu Val Ala Arg Arg Ser Ile Val Leu
    370                 375                 380

Leu Lys Asn Asp Gly Thr Leu Pro Leu Ser Lys Asn Leu Lys Lys Val
385                 390                 395                 400

Ala Val Ile Gly Pro Asn Ala Asp Asn Pro Arg Asn Leu His Gly Asp
                405                 410                 415

Tyr Ser Tyr Thr Ala His Ile Pro Ser Ile Ala Glu Gly Leu Glu Gly
                420                 425                 430

Val Lys Val Glu Glu Lys Cys Val Val Arg Thr Val Ser Ile Leu Glu
                435                 440                 445

Gly Ile Arg Asn Lys Val Ser Pro Glu Thr Glu Val Leu Tyr Ala Lys
            450                 455                 460

Gly Cys Asp Ile Ile Ser Asp Ser Lys Asp Gly Phe Ala Glu Ala Ile
465                 470                 475                 480

Glu Met Ala Lys Glu Ala Asp Val Ile Ile Ala Val Met Gly Glu Glu
                485                 490                 495

Ser Gly Leu Phe His Arg Gly Ile Ser Gly Glu Gly Asn Asp Arg Thr
            500                 505                 510

Thr Leu Glu Leu Phe Gly Val Gln Arg Asp Leu Leu Lys Glu Leu His
            515                 520                 525

Lys Leu Gly Lys Pro Ile Val Leu Val Leu Ile Asn Gly Arg Pro Gln
            530                 535                 540

Ala Leu Lys Trp Glu His Glu Asn Leu Asn Ala Ile Leu Glu Ala Trp
545                 550                 555                 560

Tyr Pro Gly Glu Glu Gly Gly Asn Ala Val Ala Asp Val Ile Phe Gly
                565                 570                 575

Asp Tyr Asn Pro Ser Gly Lys Leu Pro Ile Ser Phe Pro Ala Val Thr
                580                 585                 590

Gly Gln Ile Pro Val Tyr Tyr Asn Arg Lys Pro Ser Ala Phe Ser Asp
            595                 600                 605

Tyr Ile Asp Glu Ser Ala Lys Pro Leu Tyr Pro Phe Gly His Gly Leu
610                 615                 620

Ser Tyr Thr Thr Phe Glu Tyr Ser Asp Leu Lys Ile Ser Pro Glu Lys
625                 630                 635                 640

Val Asn Ser Leu Glu Lys Val Glu Ile Ser Phe Thr Ile Lys Asn Thr
                645                 650                 655

Gly Asn Arg Asp Gly Glu Glu Val Val Gln Leu Tyr Ile His Asp Gln
                660                 665                 670

Val Ala Ser Leu Glu Arg Pro Val Lys Glu Leu Lys Gly Phe Lys Lys
                675                 680                 685

Ile Tyr Leu Lys Pro Gly Glu Ser Lys Arg Val Thr Phe Thr Leu Tyr
            690                 695                 700

Pro Glu Gln Leu Ala Phe Tyr Asp Glu Phe Met Arg Phe Ile Val Glu
705                 710                 715                 720

Lys Gly Val Phe Glu Val Met Ile Gly Ser Ser Glu Asp Ile Arg
                725                 730                 735

Leu Met Gly Thr Phe Glu Val Leu Glu Thr Lys Val Ile Thr Glu Lys
                740                 745                 750

Arg Lys Phe Ala Ser Asp Val Lys Val Glu
            755                 760
```

The invention claimed is:

1. A thermostable β-xylosidase comprising:
   a polypeptide consisting of the amino acid sequence of SEQ ID NO: 1, and
   at least one region selected from the group consisting of a Fibronectin type III-like domain, a linker domain, a signal peptide and a tag.

2. The thermostable β-xylosidase according to claim 1, which also exhibits β-glucosidase activity.

3. A glycoside hydrolase mixture, comprising the thermostable β-xylosidase according to claim 1 and at least one other glycoside hydrolase.

4. A method for producing a lignocellulose degradation product, the method comprising generating the lignocellulose degradation product by bringing a material composed of lignocellulose containing cellulose, hemicellulose and lignin into contact with the thermostable β-xylosidase according to claim 1.

5. A method for producing a lignocellulose degradation product, the method comprising generating the lignocellulose degradation product by bringing a material composed of lignocellulose containing cellulose, hemicellulose and lignin into contact with the glycoside hydrolase mixture according to claim 3.

* * * * *